(12) United States Patent
Kasper et al.

(10) Patent No.: US 7,858,101 B2
(45) Date of Patent: Dec. 28, 2010

(54) MODIFIED STREPTOCOCCAL POLYSACCHARIDES AND USES THEREOF

(75) Inventors: Dennis L. Kasper, Charlestown, MA (US); Hilde-Kari Guttormsen, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 227 days.

(21) Appl. No.: 11/264,731

(22) Filed: Nov. 1, 2005

(65) Prior Publication Data

US 2006/0134142 A1 Jun. 22, 2006

Related U.S. Application Data

(60) Provisional application No. 60/623,907, filed on Nov. 1, 2004.

(51) Int. Cl.
*A61K 39/09* (2006.01)
*A61K 39/02* (2006.01)
*A61K 39/116* (2006.01)
*A61K 39/385* (2006.01)
*A61K 39/00* (2006.01)
*A61K 31/70* (2006.01)
*C07H 1/00* (2006.01)

(52) U.S. Cl. ............ 424/244.1; 424/234.1; 424/197.11; 424/203.1; 424/184.1; 424/194.1; 424/831; 514/23; 536/123.1

(58) Field of Classification Search .............. 424/244.1, 424/234.1, 184.1, 192.1, 194.1, 197.11, 203.1, 424/831; 514/23; 536/123.1
See application file for complete search history.

(56) References Cited

U.S. PATENT DOCUMENTS

| | | | |
|---|---|---|---|
| 4,207,414 A | 6/1980 | Kasper | |
| 4,284,537 A | 8/1981 | Beachey | |
| 4,324,887 A | 4/1982 | Kasper | |
| 4,356,170 A | 10/1982 | Jennings et al. | |
| 4,356,263 A | 10/1982 | Kasper | |
| 4,367,221 A | 1/1983 | Kasper | |
| 4,367,222 A | 1/1983 | Kasper | |
| 4,367,223 A | 1/1983 | Kasper | |
| 4,425,330 A | 1/1984 | Norcross et al. | |
| 4,438,261 A | 3/1984 | Barnett | |
| 4,619,828 A | 10/1986 | Gordon | |
| 4,757,134 A | 7/1988 | Blake et al. | |
| 4,789,735 A | 12/1988 | Frank et al. | |
| 4,902,506 A | 2/1990 | Anderson et al. | |
| 5,302,386 A | 4/1994 | Kasper et al. | |
| 5,472,696 A | 12/1995 | Boyle et al. | |
| 5,648,241 A | 7/1997 | Michel et al. | |
| 5,795,580 A | 8/1998 | Jennings et al. | |
| 5,820,860 A | 10/1998 | Michel et al. | |
| 5,843,444 A | 12/1998 | Michel et al. | |
| 5,843,461 A | 12/1998 | Jennings et al. | |
| 5,847,081 A | 12/1998 | Michel et al. | |
| 5,858,362 A | 1/1999 | Michel et al. | |
| 5,908,629 A | 6/1999 | Michel et al. | |
| 5,968,521 A | 10/1999 | Michel et al. | |
| 5,993,825 A | 11/1999 | Jennings et al. | |
| 6,355,255 B1 | 3/2002 | Cleary et al. | |
| 2004/0071729 A1 | 4/2004 | Adderson et al. | |

FOREIGN PATENT DOCUMENTS

| | | |
|---|---|---|
| WO | 94/06467 | 3/1994 |
| WO | 2004/011027 | 2/2004 |

OTHER PUBLICATIONS

Gottormsen et al. PNAS 105: 5903-5908, 2008.*
Poland GA. Vaccine 17: 1674-1679, 1999.*
Kasper et al., "Immune Response to Type III Group B Streptococcal Polysaccharide-Tetanus Toxoid Conjugate Vaccine" *J. Clin. Invest.* 98:2308-2314 (1996).
Kong et al., "Molecular Profiles of Group B Streptococcal Surface Protein Antigen Genes: Relationship to Molecular Serotypes" *J. Clin. Microbiol.* 40:620-626 (2002).
Lachenauer et al., "Mosaicism in the alpha-like protein genes of group B streptococci" *Proc. Natl. Acad. Sci. USA* 97:9630-9635 (2000).
Larsson et al., "Experimental Vaccination against Group B Streptococcus, an Encapsulated Bacterium, with Highly Purified Preparations of Cell Surface Proteins Rib and α" *Infect. Immun.* 64(9):3518-3523 (1996).
Michel et al., "Cloned Alpha and Beta C-Protein Antigens of Group B Streptococci Elicit Protective Immunity" *Infect. Immun.* 59(6):2023-2028 (1991).
Michel et al., "Large, identical, tandem repeating units in the C protein alpha antigen gene, bca, of group B streptococci" *Proc. Natl. Acad. Sci. USA* 89: 10060-10064 (1992).
Rench et al., "Neonatal sepsis caused by a new group B streptococcal serotype" *J. Pediatr.* 122(4):638-640 (1993).
Rodewald et al., "Neonatal Mouse Model of Group B Streptococcal Infection" *J. Infect. Dis.* 166(3):635-639 (1992).
Schwartz et al., "Proteins Containing Reductively Aminated Disaccharides" *Arch. Biochem. Biophys.* 181:542-549 (1977).
Spellerberg et al., "Lmb, a Protein with Similarities to the LraI. adhesion Family, Mediates Attachment of *Streptococcus agalactiae* to Human Laminin" *Infect. Immun.* 67(2):871-878 (1999).
Tettelin et al., "Complete genome sequence and comparative genomic analysis of an emerging human pathogen, serotype V *Streptococcus agalactiae*" *Proc. Natl. Acad. Sci. USA* 99(19):12391-12396 (2002).
Wang et al., "Construction of designer glycoconjugate vaccines with size-specific oligosaccharide antigens and site-controlled coupling" *Vaccine* 21(11-12):1112-1117 (2003).

(Continued)

*Primary Examiner*—S. Devi
(74) *Attorney, Agent, or Firm*—Fish & Richardson P.C.

(57) ABSTRACT

Modified streptococcal polysaccharides and methods of using the modified polysaccharides are provided herein.

15 Claims, 30 Drawing Sheets

OTHER PUBLICATIONS

Wästfelt et al., "Identification of a Family of Streptococcal Surface Proteins with Extremely Repetitive Structure" *J. Biol. Chem.* 271(31):18892-18897 (1996).

Wessels et al., "Immunogenicity and protective activity in animals of a group B *Streptococcus* type V polysaccharide-tetanus toxoid conjugate vaccines" *J. Infect. Dis.*171:879-884 (1995).

Wessels et al., "Immunogenicity in Animals of a Polysaccharide-Protein Conjugate Vaccine against Type III Group B *Streptococcus*" *J. Clin. Invest.* 86:1428-1433 (1990).

Wessels et al., "Structural Determination and Immunochemical Characterization of the Type V Group B *Streptococcus* Capsular Polysaccharide" *J. Biol Chem.* 266(11):6714-6719 (1991).

Zaleznik et al., "Invasive Disease Due to Group B Streptococcus in Pregnant Women and Neonates from Diverse Population Groups" *Clin. Infect Dis.* 30(2):276-281 (2000).

Palazzi et al., "Use of Type V Group B Streptococcal Conjugate Vaccine in Adults 65-85 Years Old" *J. Infect. Dis.* 190:558-564 (2004).

Adderson et al., "Subtractive Hybridization Identifies a Novel Predicted Protein Mediating Epithelial Cell Invasion by Virulent Serotype III Group B *Streptococcus agalactiae*" *Infect. Immun.* 71(12):6857-6863 (2003).

Anthony et al., "The Emergence of Group B Streptococci in Infections of the Newborn Infant" *Annu. Rev. Med.* 28:355-369 (1977).

Baker et al., "Immune Response of Healthy Women to 2 Different Group B Streptococcal Type V Capsular Polysaccharide-Protein Conjugate Vaccines" *J. Infect. Dis.* 189:1103-1112 (2004).

Baker et al., "Safety and Immunogenicity of Capsular Polysaccharide-Tetanus Toxoid Conjugate Vaccines for Group B Streptococcal Types Ia and Ib"*J. Infect. Dis.* 179:142-150 (1999).

Baker et al., "Use of Capsular Polysaccharide—Tetanus Toxoid Conjugate Vaccine for Type II Group B *Streptococcus* in Healthy Women" *J. Infect. Dis.* 182:1129-1138 (2000).

Baker, "Group B Streptococcal Infections" *Adv. Intern. Med.* 25:475-501 (1980).

Blumberg et al., "Invasive group B streptococcal disease: The emergence of serotype V" *J. Infect. Dis.* 173:365-373 (1996).

Deng et al., "Characterization of the Linkage between the Type III Capsular Polysaccharide and the Bacterial Cell Wall of Group B *Streptococcus*" *J. Biol. Chem.* 275(11):7497-7504 (2000).

Dillion et al., "Group B streptococcal carriage and disease: A 6 year prospective study" *J. Pediatr.* 110(1):31-36 (1987).

Elliott et al., "Sudden increase in isolation of group B streptococci, serotype V, is not due to emergence of a new pulsed-field gel electrophoresis type" *J. Clin. Microbiol.* 36:2115-2116 (1998).

Farley et al., "Group B streptococcal disease in nonpregnant adults" *Clin. Infect. Dis.* 33:556-561 (2001).

Ferrieri, "Surface-Localized Protein Antigens of Group B Streptococci" *Rev. Infect. Dis.* 10(Suppl. 2):S363-S366 (1988).

Greenberg et al., "Group B streptococcus serotype V" *J. Pediatr.* 123(3):494-495 (1993).

Harrison et al., "Serotype distribution of invasive group B streptococcal isolates in Maryland: Implications for vaccine formulation" *J. Infect. Dis.* 177:998-1002 (1998).

Heden et al., "Molecular characterization of IgA receptor from group B streptococci: sequence of the gene, identification of a proline-rich region with unique structure and isolation of N-terminal fragments with IgA-binding capacity" *Eur. J. Immunol.* 21(6):1481-1490 (1991).

Hervás et al., "Neonatal sepsis caused by a new group B streptococcal serotype (type V)" *J. Pediatr.* 123(5):839 (1993).

Jelinkova et al., "Worldwide distribution of two new serotypes of group B streptococci: type IV and provisional type V" *J. Clin. Microbiol.* 21:361-362 (1985).

Baker et al., "Group B streptococcal conjugate vaccines," Archives of Disease in Childhood 88(5):375-378 (2003).

Molinari et al., "Effects of some capsular components on pathogenicity of type IV and provisional type V group B streptococci," FEMS Microbiology Letters 41(1):69-72 (1987).

\* cited by examiner

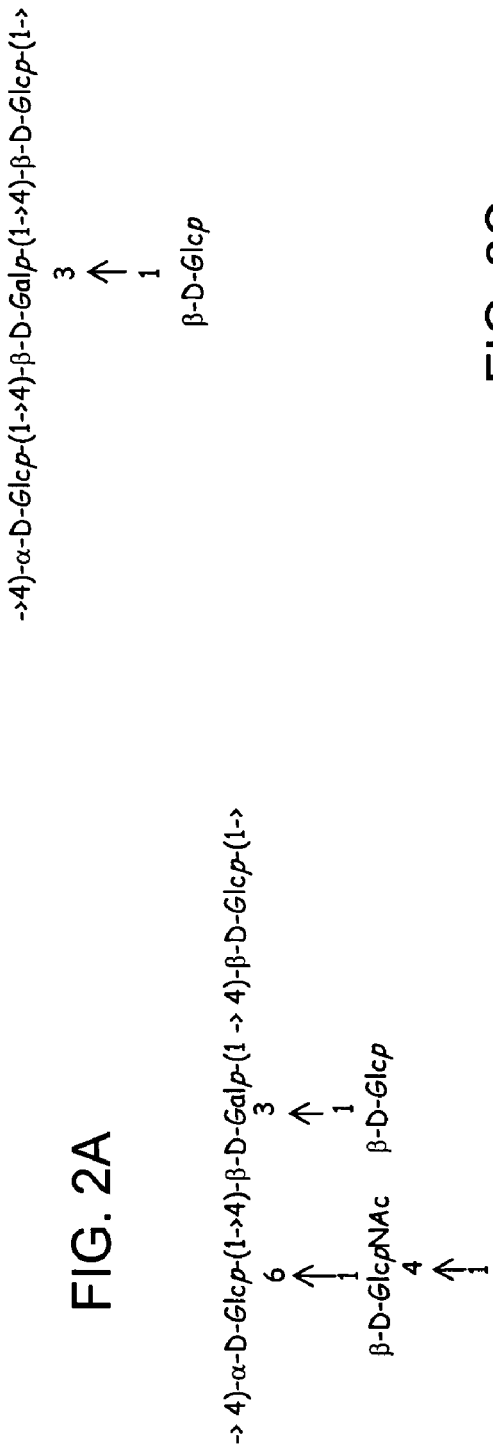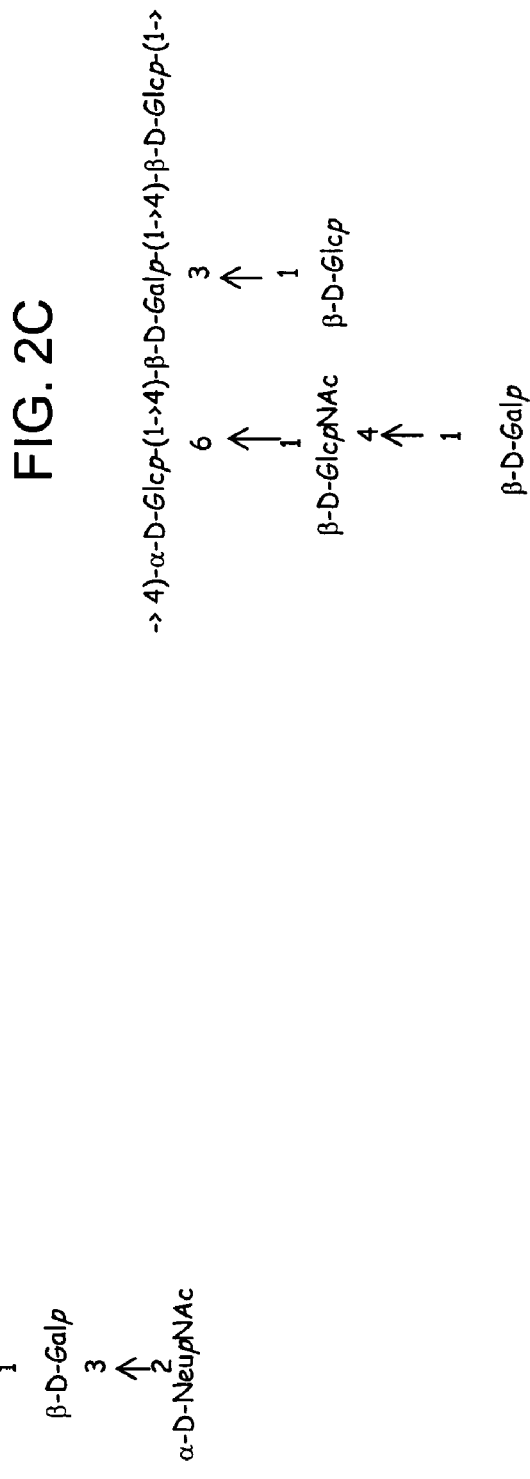

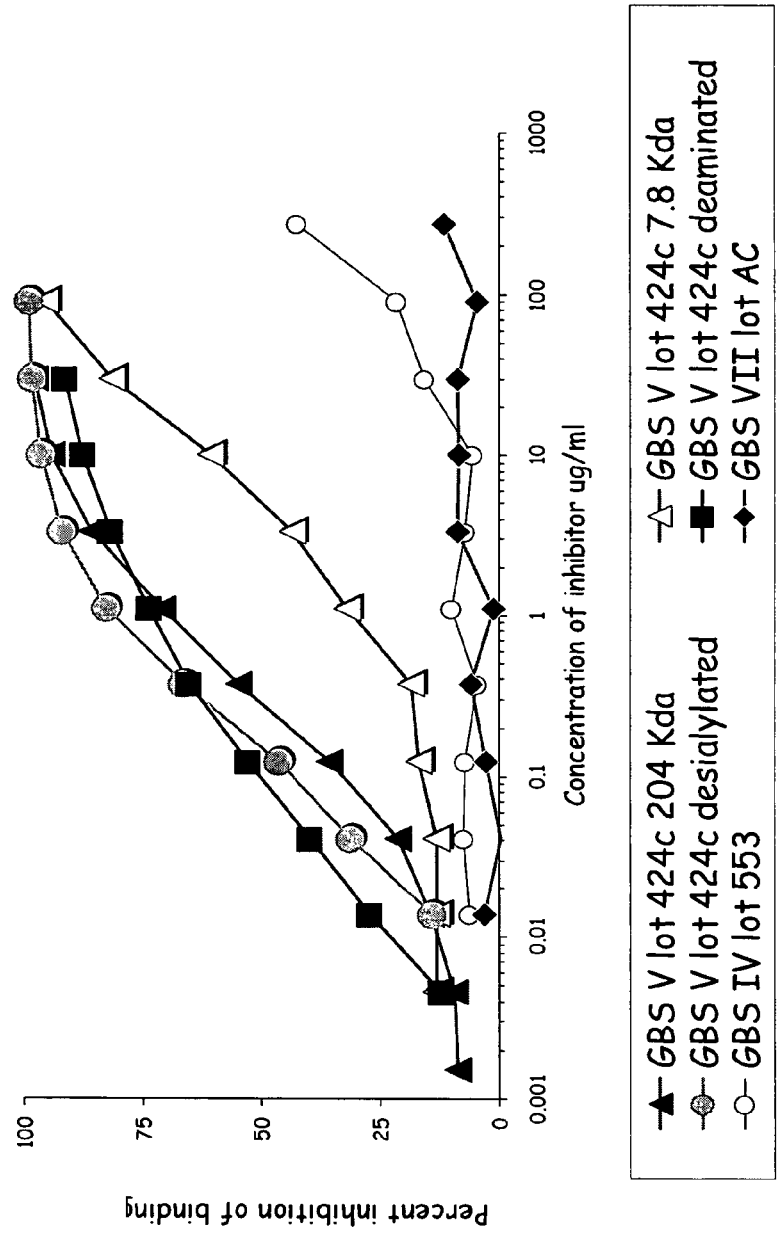

Inhibition of binding by IgM fraction human V-TT-induced V-specific antibodies by GBS V and modified forms thereof

FIG. 5

Killing of GBS V Bacteria by Human V-specific Antibodies

Opsonophagocytic Killing of GBS V by V-TT Induced Antibodies in the Presence of Type V and Desialylated Type V Polysaccharides

FIG. 7

Inhibition of binding by IgG murine monoclonal V-TT-induced V-specific antibody by GBS V and modified forms thereof

FIG. 14

Isotype-switched Antibodies
Induced by GBS Type V-TT Vaccine

Isotype switched antibodies hu after 1°   hu after 2°   primates after 1°   primates after 2°

Isotype switching to V-IgG
(Percentage of V IgG + V IgM)

Killing of GBS V Bacteria by Macaque Antibodies

FIG. 22

V-specific IgA antibodies in Macaques after
two doses of GBS V desialylated -TT (50 µg PS i.m.)

Specificity of GBS desialylated GBS V-induced IgM antibodies in Macaque #

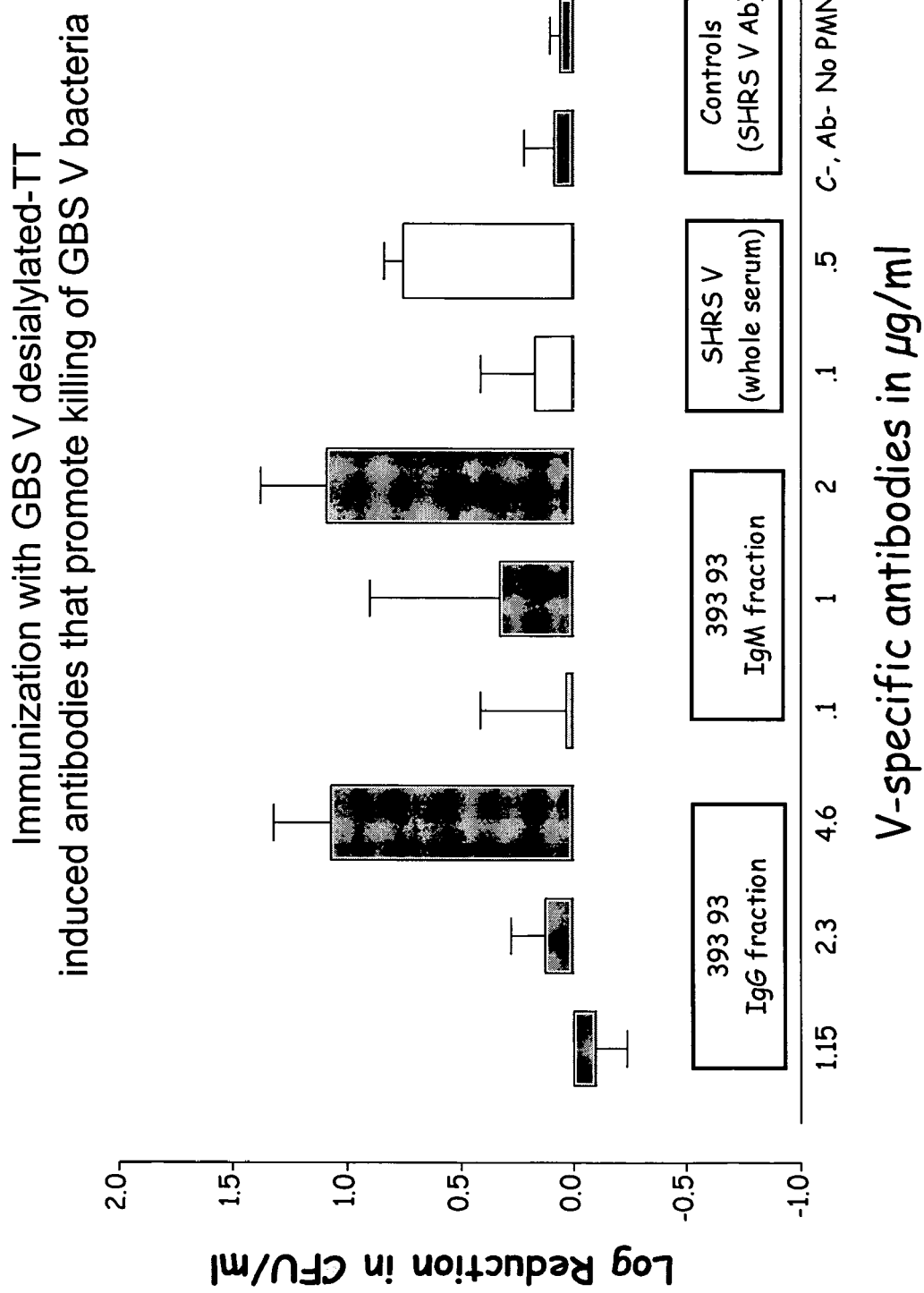

V-TT 0.625 μg PS alum as adjuvant: V IgG response

MODIFIED STREPTOCOCCAL POLYSACCHARIDES AND USES THEREOF

CROSS-REFERENCE TO RELATED APPLICATIONS

This application claims the benefit of priority of U.S. Ser. No. 60/623,907, filed Nov. 1, 2004, the contents of which are hereby incorporated by reference in their entirety.

The work described herein was funded, in part, through a grant from the National Institutes of Health (Grant Nos. R37 AI23339 and N01-AI-25495). The United States government may, therefore, have certain rights in the invention.

TECHNICAL FIELD

This invention relates to compositions that include bacterial polysaccharides and modified polysaccharides, and more particularly to uses of the polysaccharides for inducing immune responses in mammals.

BACKGROUND

Group B streptococci are a major cause of neonatal sepsis and meningitis in the United States and other parts of the world (Anthony and Okada, *Annu Rev Med.*, 28:355-69, 1977; Baker, *Adv Intern Med.*, 25:475-501, 1980; Dillion et al., *J Pediatr.*, 110(1):31-6, 1987). Prior to the 1990's, virtually all invasive group B streptococcal (GBS) infections were caused by serotypes Ia, Ib, II, and III. Reports of infection of newborn infants by a new serotype, type V, appeared in the pediatric literature in the 1990's (Greenberg et al., *J Pediatr.*, 123(3):494-5, 1993; Hervas and Benedi, *J Pediatr.*, 123(5): 839, 1993; Rench and Baker, *J Pediatr.*, 122(4):638-40, 1993). Infections caused by type V GBS were clearly becoming more common by the mid-1990's, and this serotype is now recognized as a common cause of infections in newborn infants and pregnant women (Zaleznik et al., *Clin Infect Dis.*, 30(2):276-81, 2000). The capsular polysaccharide of type V GBS has structural features in common with other GBS capsular polysaccharides (CPS) but it is antigenically distinct (Wessels et al., *J Biol Chem.*, 266(11):6714-9, 1991).

SUMMARY

The invention is based, in part, on the observation that the immunogenicity of bacterial polysaccharides can be enhanced by modifying the structure of the polysaccharides, e.g., to reveal an immunodominant epitope on the polysaccharides. We have found that GBS type V capsular polysaccharides (GBS V CPS or GBS V PS) which are chemically modified such that one or more side chain residues of the polysaccharide is removed elicit potent IgG responses in primates.

In one aspect, the invention features an antigenic composition that includes a modified bacterial polysaccharide. The modified bacterial polysaccharide can be a form of the polysaccharide that is structurally modified to reveal an immunogenic epitope, e.g., an immunodominant epitope. Modification of the polysaccharide can enhance immunogenicity of the polysaccharide in a host organism and/or stimulate an immune response which is more effective for protecting the host organism than that induced by a non-modified (e.g., native) form of the polysaccharide. Modifications that can enhance immunogenicity include modifications which remove one or more sidechain saccharide residues from the backbone residues of the polysaccharide.

In one embodiment, the modified polysaccharide induces an antibody response, e.g., an enhanced antibody response as compared to a native form of the polysaccharide, e.g., a protective antibody response in a mammal (e.g., a primate). In one embodiment, the polysaccharide induces an IgG response. The polysaccharide can be physically associated (e.g., covalently associated) with a carrier moiety, such as a polypeptide (e.g., a bacterial polypeptide). The modified polysaccharides can include features described herein (e.g., the modified polysaccharide can be, for example, a modified group B *streptococcus* (GBS) type V polysaccharide, e.g., which is modified such that one or more sidechain saccharides are removed, e.g., the modified polysaccharide is a deaminated GBS type V polysaccharide or a desialylated GBS type V polysaccharide).

In another aspect, the invention features an antigenic composition that includes: (a) a modified GBS type V polysaccharide; and (b) a moiety that is physically (e.g., covalently) associated with the polysaccharide. The polysaccharide can be modified by a treatment that removes one or more side chain saccharide residues from the polysaccharide. For example, the polysaccharide is treated under conditions that remove sidechain-terminal sialic acid residues from the polysaccharide, e.g., by treatment under mildly acidic conditions or with neuraminidase. In one embodiment, the polysaccharide is a desialylated GBS type V polysaccharide. In one embodiment, the polysaccharide is modified by treatment under conditions that remove trisaccharide sidechains from the backbone of the polysaccharide. The polysaccharide can be modified by sequential desialylation, deacetylation, and deamination. In one embodiment, the polysaccharide is a deaminated GBS type V polysaccharide.

In some embodiments, the modified polysaccharide is produced in bacteria (e.g., a GBS V bacteria) which are genetically modified so as to synthesize the polysaccharide in a modified form (e.g., the bacteria is deficient for expression of an enzyme that adds side chains to the polysaccharide, or the bacteria expresses or overexpresses an enzyme that removes side chain(s) from the polysaccharide).

The moiety with which the modified GBS polysaccharide is associated is, for example, a compound that enhances binding of the modified polysaccharide to an antigen presenting cell, such as a polypeptide, e.g., a bacterial polypeptide, e.g., a cell-surface or secreted bacterial polypeptide. Polypeptides can be directly linked to the polysaccharide or via a linking agent. In various embodiments, the polypeptide is a GBS polypeptide, e.g., a cell-surface or secreted GBS polypeptide. In various embodiments, the GBS polypeptide is selected from the group consisting of: a GBS C protein alpha polypeptide, a GBS C protein beta polypeptide, an epsilon polypeptide, an R protein, an alpha-like protein, a surface protein of group b *streptococcus* 1 (spb1), an spb2, laminin binding protein (Lmb), a C5a peptidase, a matrix adhesion (Ema) polypeptides, and antigenic fragments and variants thereof. The GBS polypeptide may be a polypeptide of GBS type Ia, Ib, II, III, IV, V, VI, or VIII. In one embodiment, the polypeptide is a polypeptide encoded by a gene product identified in the sequence of the GBS V genome in Tettelin et al., *Proc Natl Acad Sci USA*, 99(19):12391-6, 2002, the contents of which are herein incorporated by reference in their entirety.

In one embodiment, the polypeptide is a bacterial toxin or a toxoid, e.g., a tetanus toxoid, a diphtheria toxoid, a diphtheria mutant protein cross-reactive material (CRM197), or an antigenic fragment thereof.

The composition can include more than one type of carrier moiety. For example, the modified polysaccharide can be linked to two, three, four, or five different polypeptides, e.g., two or more bacterial polypeptides, e.g., a bacterial toxoid and a GBS C protein alpha.

The polysaccharide component of the composition can be at least 1 kiloDalton (kD), 5 kD, 10 kD, 15 kD, 20 kD, 25 kD, or 50 kD. The composition can have an amount of between 0.1 and 500 µg of the polysaccharide, e.g., between 0.5 and 100 µg, 1 and 50 µg, or 5 and 25 µg.

In one embodiment, the composition further includes a pharmaceutically acceptable carrier. In one embodiment, the composition further includes an adjuvant, e.g., alum.

The composition can further include a second polysaccharide, e.g., a polysaccharide of another GBS serotype or of a non-GBS bacteria, e.g., one or more of a GBS type Ia, Ib, II, III, IV, VI, VII, or VIII polysaccharide, in addition to the modified GBS type V polysaccharide.

In another aspect, the invention features a method for eliciting an immune response in a mammal. The method includes, for example, administering to the mammal a composition comprising: (a) a modified bacterial polysaccharide, e.g., a modified group B *streptococcus* (GBS) type V polysaccharide; and, optionally, (b) a moiety that is physically associated (e.g., covalently associated) with the polysaccharide; thereby eliciting an immune response in the mammal.

The polysaccharide can be modified by treatment under conditions that remove sidechain-terminal sialic acid residues from the polysaccharide, e.g., a desialylated GBS type V polysaccharide. The polysaccharide can be modified by treatment under conditions that remove trisaccharide sidechains from the backbone of the polysaccharide The polysaccharide can be modified by sequential desialylation, deacetylation, and deamination. In one embodiment, the polysaccharide is a deaminated GBS type V polysaccharide.

The moiety with which the modified GBS polysaccharide is associated can be a polypeptide, e.g., a bacterial polypeptide, e.g., a cell-surface or secreted bacterial polypeptide. In various embodiments, the polypeptide is a GBS polypeptide, e.g., a cell-surface or secreted GBS polypeptide. In various embodiments, the GBS polypeptide is selected from the group consisting of: a GBS C protein alpha polypeptide, a GBS C protein beta polypeptide, an epsilon polypeptide, an R protein, an alpha-like protein, a surface protein of group b *streptococcus* 1 (spb1), an spb2, laminin binding protein (Lmb), a C5a peptidase, a matrix adhesion (Ema) polypeptides, and antigenic fragments and variants thereof. The GBS polypeptide may be a polypeptide of GBS type Ia, Ib, II, III, IV, V, VI, VI, or VIII.

In one embodiment, the polypeptide is a bacterial toxin or a toxoid, e.g., a tetanus toxoid, a diphtheria toxoid, a diphtheria mutant protein cross-reactive material (CRM197), or an antigenic fragment thereof.

The composition can include more than one type of carrier moiety. For example, the modified polysaccharide can be linked to two, three, four, or five different polypeptides, e.g., two or more bacterial polypeptides, e.g., a bacterial toxoid and a GBS C protein alpha.

The polysaccharide component of the composition can be at least 1 kiloDalton (kD), 5 kD, 10 kD, 15 kD, 20 kD, 25 kD, or 50 kD.

In one embodiment, the composition further includes a pharmaceutically acceptable carrier. In one embodiment, the composition further includes an adjuvant, e.g., alum.

The composition can further include a second polysaccharide, e.g., a polysaccharide of another GBS serotype or of a non-GBS bacteria, e.g., one or more of a GBS type Ia, Ib, II, III, IV, VI, VII, or VIII polysaccharide, in addition to the modified GBS type V polysaccharide.

The composition can be administered to the subject once, or two or more times. In one embodiment, an amount of the composition containing between 0.1 and 500 µg of the polysaccharide, e.g, between 25 and 100 µg, of the polysaccharide is administered to the mammal.

The method can elicit an antibody response in the mammal, e.g., an enhanced antibody response, e.g., an IgG antibody response, e.g., an IgM antibody response, in the mammal. In one embodiment, the method elicits a protective response in the mammal. The method can further include evaluating an immune response to GBS bacteria in the mammal (e.g., evaluating a humoral immune response and/or a cell-mediated immune response).

In one embodiment, the mammal is at risk for infection with GBS bacteria, e.g., the mammal is immunocompromised or at risk for becoming immunocompromised, or is elderly.

In one embodiment, mammal is a primate, e.g., a human or a monkey. In one embodiment, the composition is administered to a human over 10, 20, 30, 40, 50, 60, 65, 70, 75, or 80 years of age.

In one embodiment, the mammal is pregnant.

In yet another aspect, the invention features a method of providing antibodies to a neonate. The method can include, for example, administering to a pregnant female an antigenic composition comprising: (a) a modified group B *streptococcus* (GBS) type V polysaccharide; and, optionally, (b) a moiety that is physically associated with the polysaccharide. The composition can be a composition described herein.

In another aspect, the invention features a method for preparing an immunogenic composition. The method includes, for example, providing a purified GBS V polysaccharide; and treating the polysaccharide under conditions that modify the structure of the polysaccharide. In one embodiment, the polysaccharide is modified under conditions that remove one or more residues of a sidechain of the polysaccharide, e.g., the polysaccharide is modified under conditions that remove a sidechain-terminal sialic acid residue of the polysaccharide, or the polysaccharide is modified under conditions that remove the trisaccharide sidechain of the polysaccharide.

The invention also features a composition that includes antisera obtained by a method that includes providing a purified GBS V polysaccharide; and treating the polysaccharide under conditions that modify the structure of the polysaccharide. In one embodiment, the polysaccharide is modified under conditions that remove one or more residues of a sidechain of the polysaccharide, e.g., the polysaccharide is modified under conditions that remove a sidechain-terminal sialic acid residue of the polysaccharide, or the polysaccharide is modified under conditions that remove the trisaccharide sidechain of the polysaccharide.

Antibodies prepared by methods described herein can be prepared and administered to subjects, e.g., subjects at risk for or exposed to GBS. In one embodiment, one or more mammals (e.g., humans) are administered a composition comprising (a) a modified bacterial polysaccharide, e.g., a modified group B *streptococcus* (GBS) type V polysaccharide; and (b) a moiety that is physically associated (e.g., covalently associated) with the polysaccharide. Samples that include antibodies (e.g., antisera) are isolated from the subject(s). Multiple samples may be pooled. The antisera are administered to a second mammal (e.g., a human), in an amount sufficient to decrease a symptom of infection or the degree of infection by GBS in the subject.

"Modified bacterial polysaccharide" refers to a bacterial polysaccharide that is modified so as to have a structure that is distinct from a native form of the polysaccharide (i.e., the natural form of the polysaccharide found on the bacteria).

"Purified" refers to polysaccharide material substantially separated from the various protein and lipid components naturally associated with the polysaccharide. Residual foreign components in the purified oligosaccharide do not interfere with the use of the purified material as an antigen. The term "purified" does not exclude synthetic oligosaccharide preparations retaining artifacts of their synthesis; nor does it exclude preparations that include some impurities, so long as the preparation exhibits reproducible data, for example, molecular weight, sugar residue content, sugar linkages, chromatographic response, and immunogenic behavior.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). The composition, i.e., modified GBS V CPS-conjugate composition may be provided in a substance that protects it from the action of acids and other natural compounds that may inactivate it.

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Ser. No. 60/623,907 is incorporated by reference in its entirety for all purposes.

DESCRIPTION OF DRAWINGS

FIG. 2A is a graphic depiction of the structure of the heptasaccharide repeating unit of GBS type V capsular polysaccharide.

FIG. 2B is a graphic depiction of the structure of the deaminated form of GBS type V capsular polysaccharide.

FIG. 2C Is a graphic depiction of the structure of the desialylated form of GBS type V capsular polysaccharide.

FIG. 3 is a graph depicting the inhibition of binding by IgG fraction of human serum of subjects immunized with a GBS type V polysaccharide-tetanus toxoid (GBS V-TT) conjugate vaccine to native GBS type V in the presence of: (1) native type V polysaccharide consisting of a polymer of approximately 200 repeat units (filled triangles); (2) chemically modified type V polysaccharide representing reduced size type V oligosaccharide (OS) obtained by ozone treatment of the PS (open triangles); (3) full length desialylated type V PS (filled circles); (4) deaminated type V PS which contains the type V backbone with the one-sugar side-chain (filled squares); (5) type V PS without the single sugar sidechain (which is identical to the structure of GBS type VII PS) (diamonds); and (6) GBS type IV PS (open circles).

FIG. 5 is a bar graph depicting killing of GBS V bacteria by human GBS type V-specific antibodies. Results for the IgG fraction, IgM fraction, and whole serum are shown in black, striped, and white bars, respectively. Results for control serum are shown by gray bars.

FIG. 7 is a graph depicting the inhibition of binding by a GBS V-TT-induced murine monoclonal IgG to native GBS V in the presence of: (1) native GBS V polysaccharide (filled triangles); (2) chemically modified GBS V polysaccharide representing reduced size GBS V oligosaccharide (OS) obtained by ozone treatment of the PS (open triangles); (3) GBS IV PS (open circles); (4) GBS V PS without the single sugar sidechain (which is identical to the structure of GBS type VII PS) (open squares); (5) desialylated type V PS (filled circles); and (6) deaminated type V PS which contains the type V backbone with the one-sugar side-chain (filled squares).

FIG. 14 is a graph depicting levels of isotype-switched GBS V-specific antibodies in humans (hu) and macaques (primates) after primary and secondary immunizations with a GBS V-TT glycoconjugate vaccine.

full length Pneumococcal type 14 PS (i.e. desialylated type III PS, filled squares); (4) GBS Ia PS which contains the same three-sugar side-chains as type III (open circles); (5) GBS III-HSA (identical to the coating antigen; filled triangles); and (6) human serum albumin (HSA; crosses).

Figure 18:
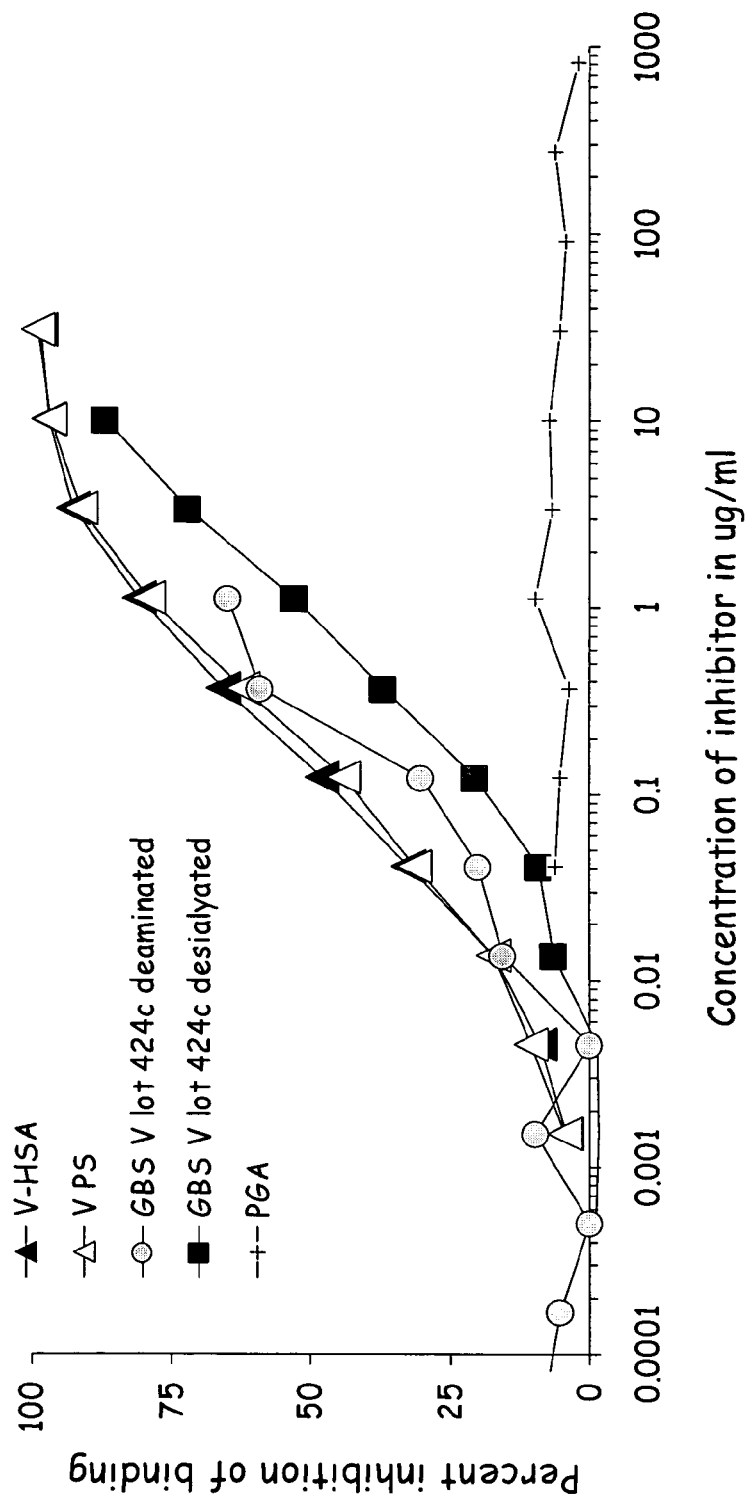

FIG. 18 is a graph depicting the inhibition of binding by IgG antibodies of macaque # 120 92 to GBS V in the presence of: (1) native type V polysaccharide consisting of a polymer of approximately 200 repeat units conjugated to HSA (filled black triangles); (2) unconjugated GBS V (white triangles); (3) desialylated type V PS (filled squares); (4) deaminated type V PS which contains the type V backbone with the one-sugar side-chain (circles); and (5) PGA (crosses).

Figure 19:
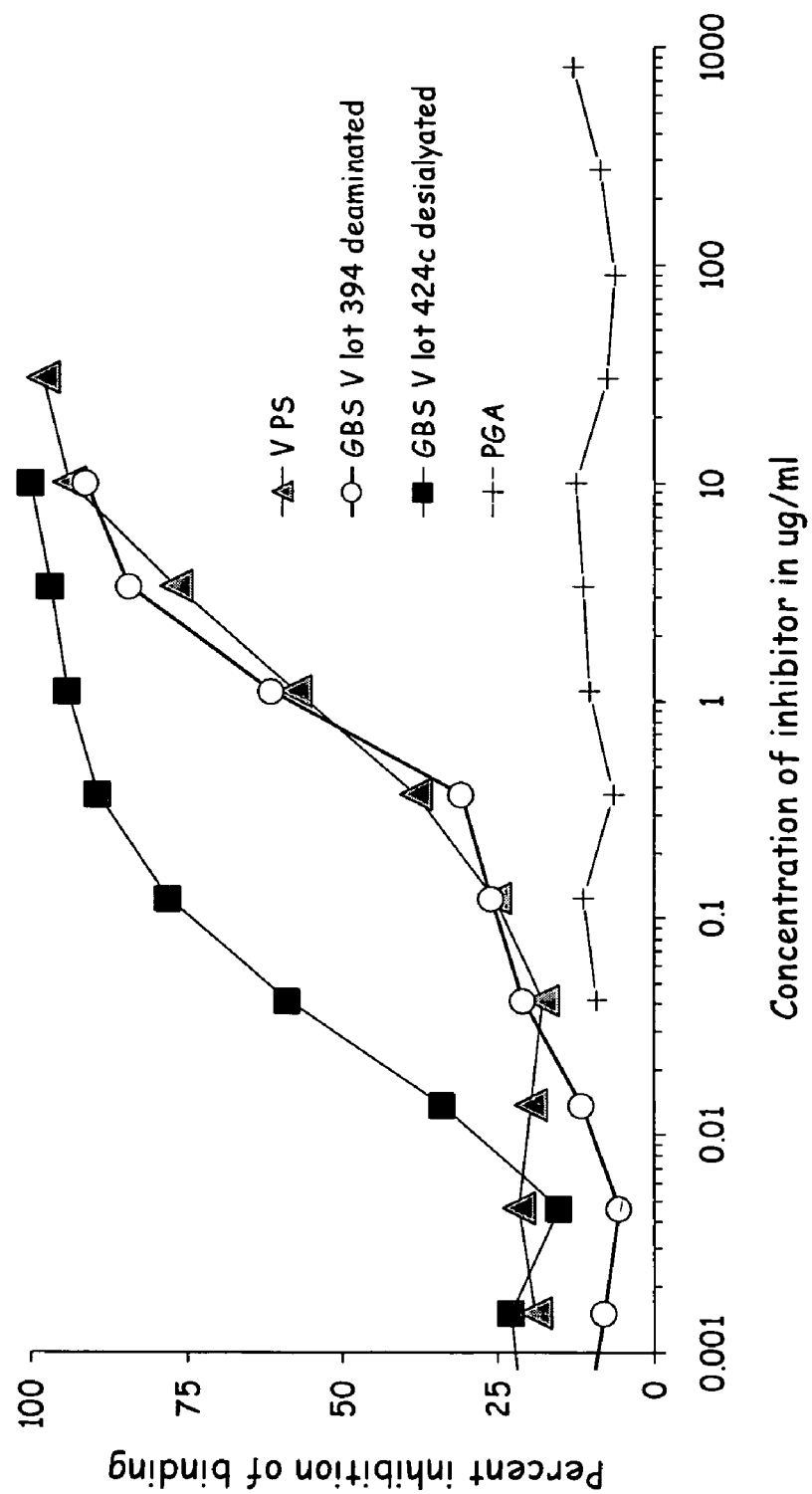

FIG. 19 is a graph depicting the inhibition of binding by IgG antibodies of macaque # 256 89 to GBS V in the presence of: (1) native type V polysaccharide (filled triangles); (2) desialylated type V PS (filled squares); (3) deaminated type V PS which contains the type V backbone with the one-sugar side-chain (circles); and (4) PGA (crosses).

Figure 20:
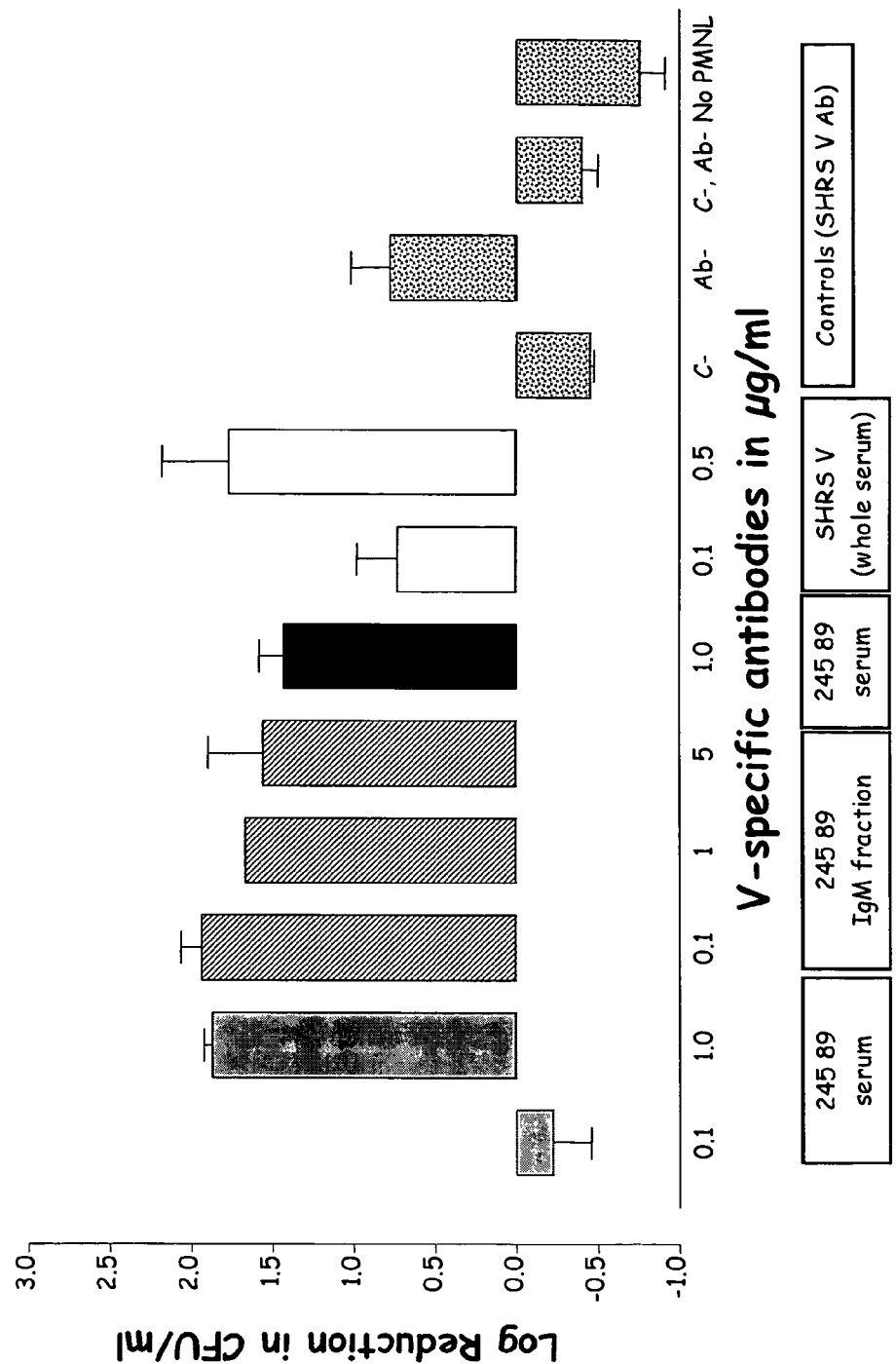

FIG. 20 is a bar graph depicting killing of GBS V bacteria by various concentrations of IgM fraction and serum from macaque #245 89 and control sera.

Figure 21:
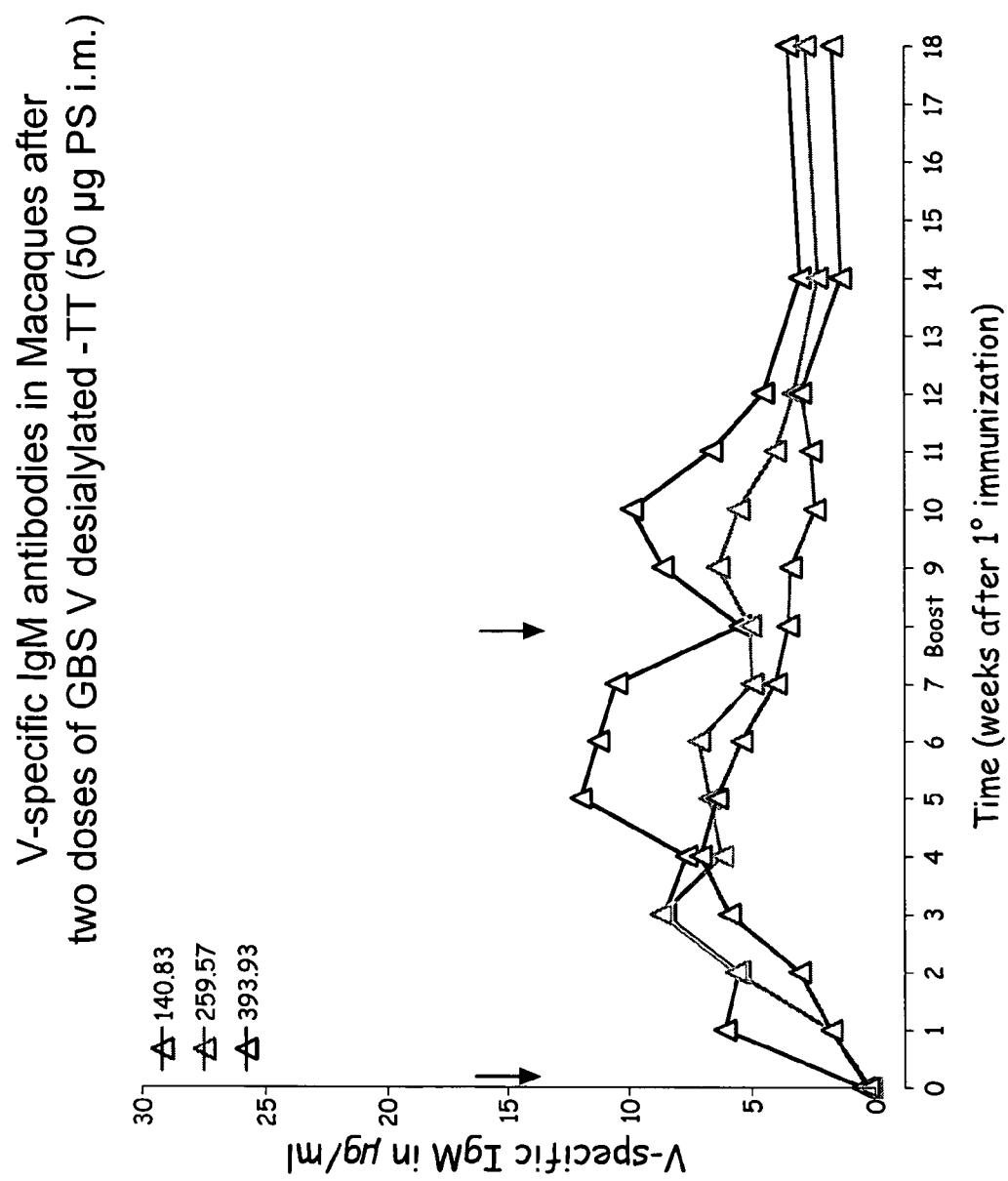

FIG. 21 is a graph depicting levels of GBS V-specific IgM antibodies in three monkeys immunized with a desialylated GBS V-TT vaccine.

FIG. 22 is a graph depicting levels of GBS V-specific IgA antibodies in three monkeys immunized with a desialylated GBS V-TT vaccine.

Figure 23:
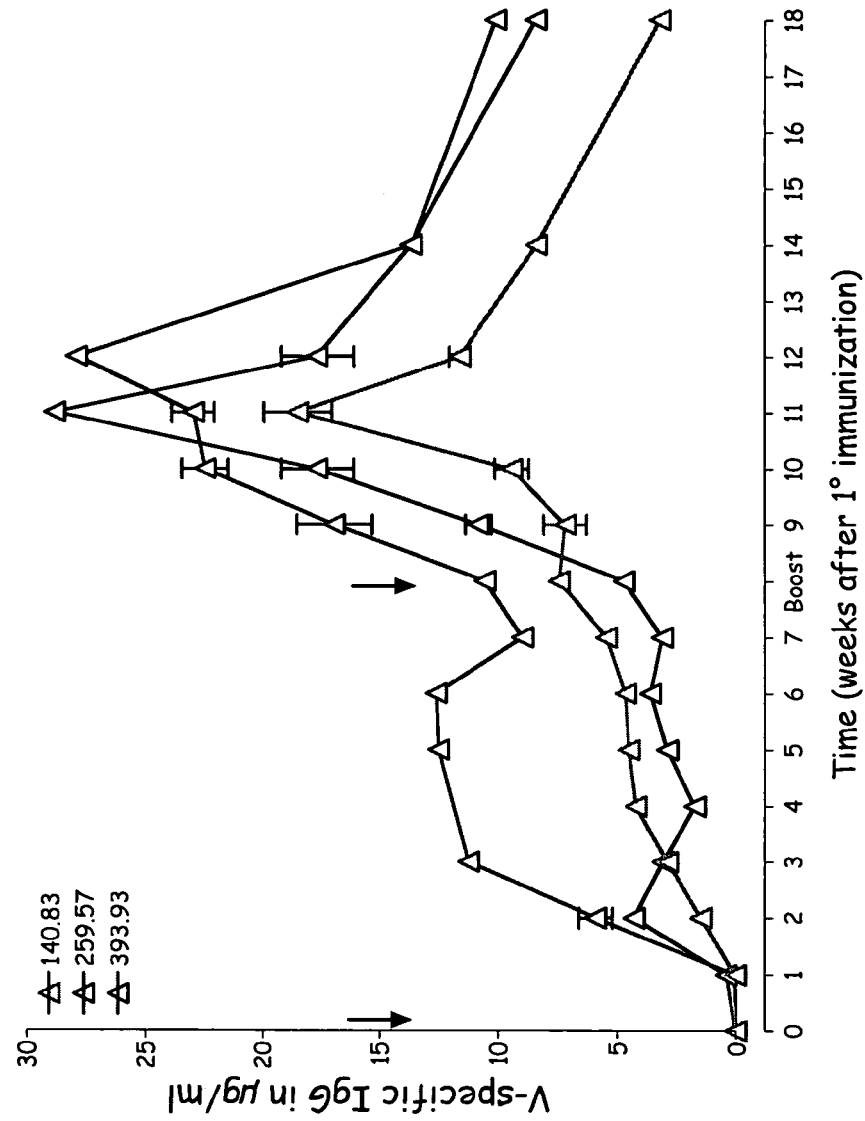

FIG. 23 is a graph depicting levels of GBS V-specific IgG antibodies in three monkeys immunized with a desialylated GBS V-TT vaccine.

Figure 24:
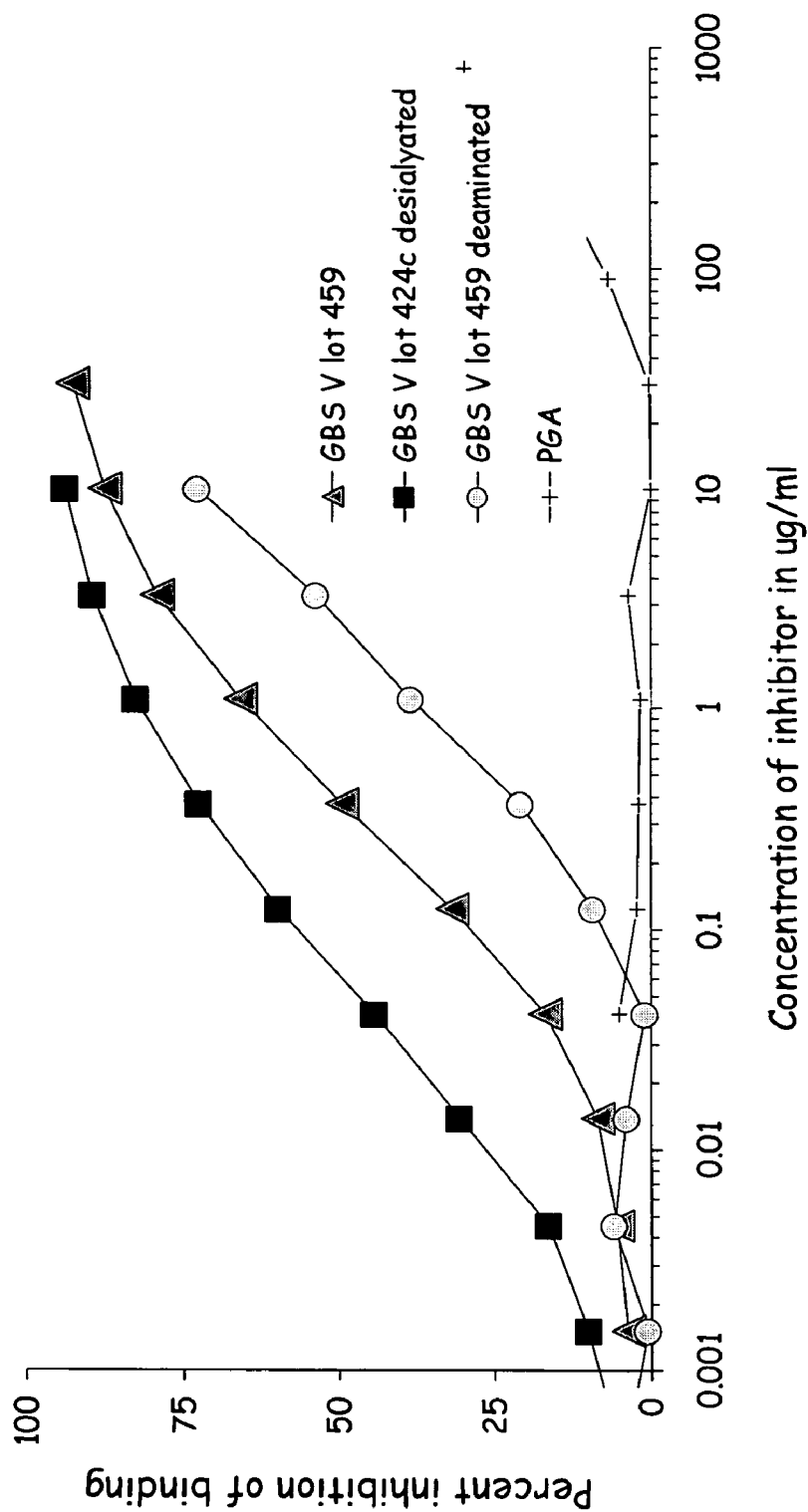

FIG. 24 is a graph depicting inhibition of binding of GBS V-specific IgG antibodies from macaque # 259 87 in the presence of: deaminated (circles), desialylated (squares), and native GM V PS (triangles).

Figure 25:
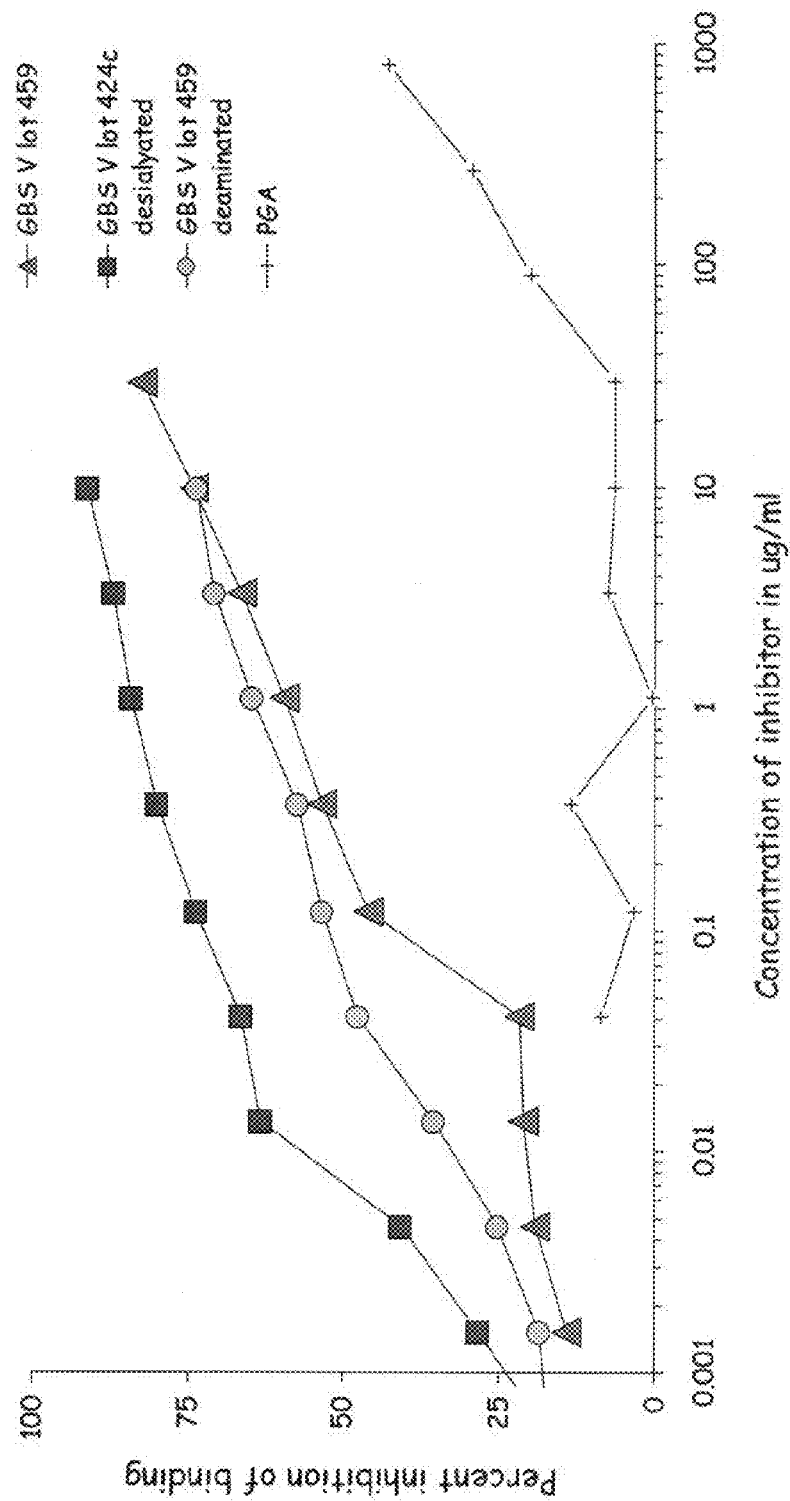

FIG. 25 is a graph depicting inhibition of binding of GBS V-specific IgM antibodies from macaque # 259 87 in the presence of: deaminated (circles), desialylated (squares), and native GBS V PS (triangles).

FIG. 26 is a bar graph killing of GBS V bacteria by various concentrations of IgM fraction, IgG fraction, and serum from macaque # 393 93.

Figure 27A:
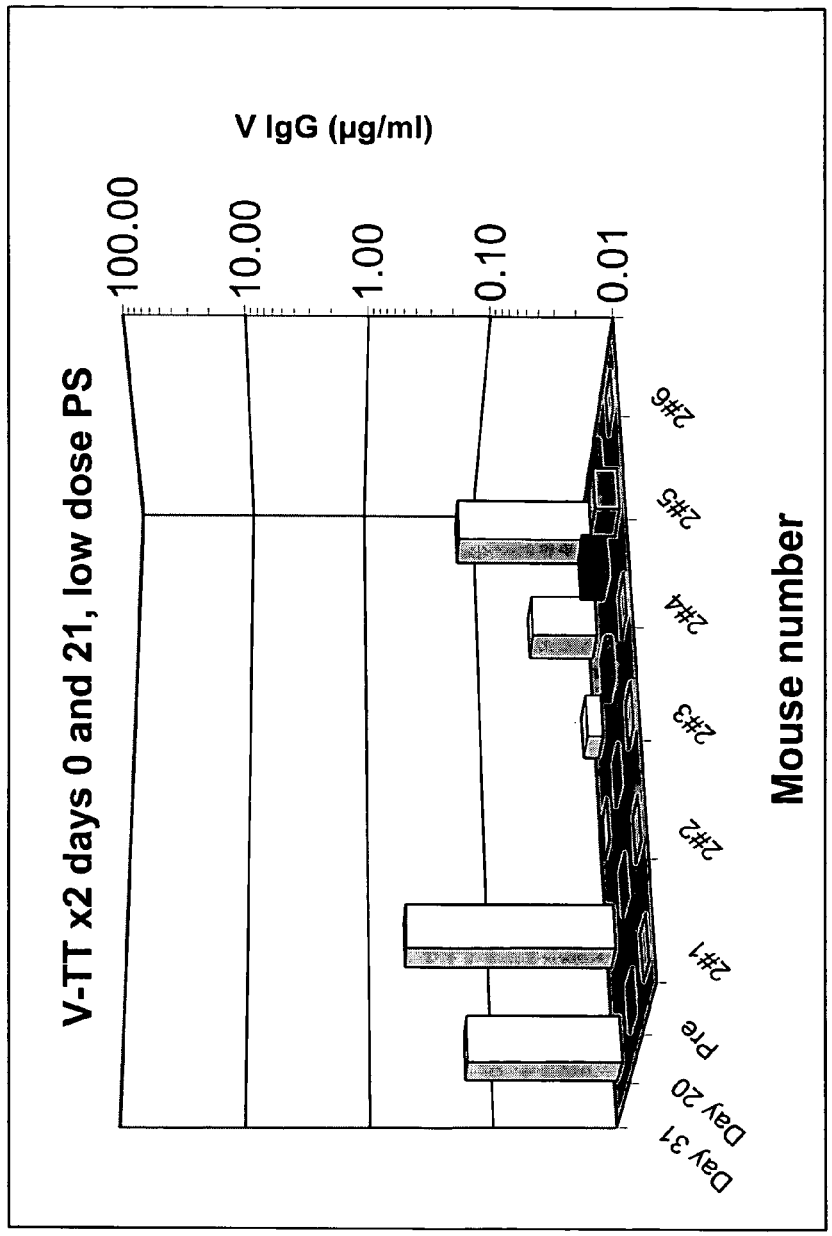

FIG. 27A is a graph depicting the levels of V-specific IgG induced in six different mice immunized with 0.625 µg per dose of a GBS V-TT conjugate vaccine. Results for sera obtained prior to immunization, at day 20, and at day 31 are shown.

Figure 27B:
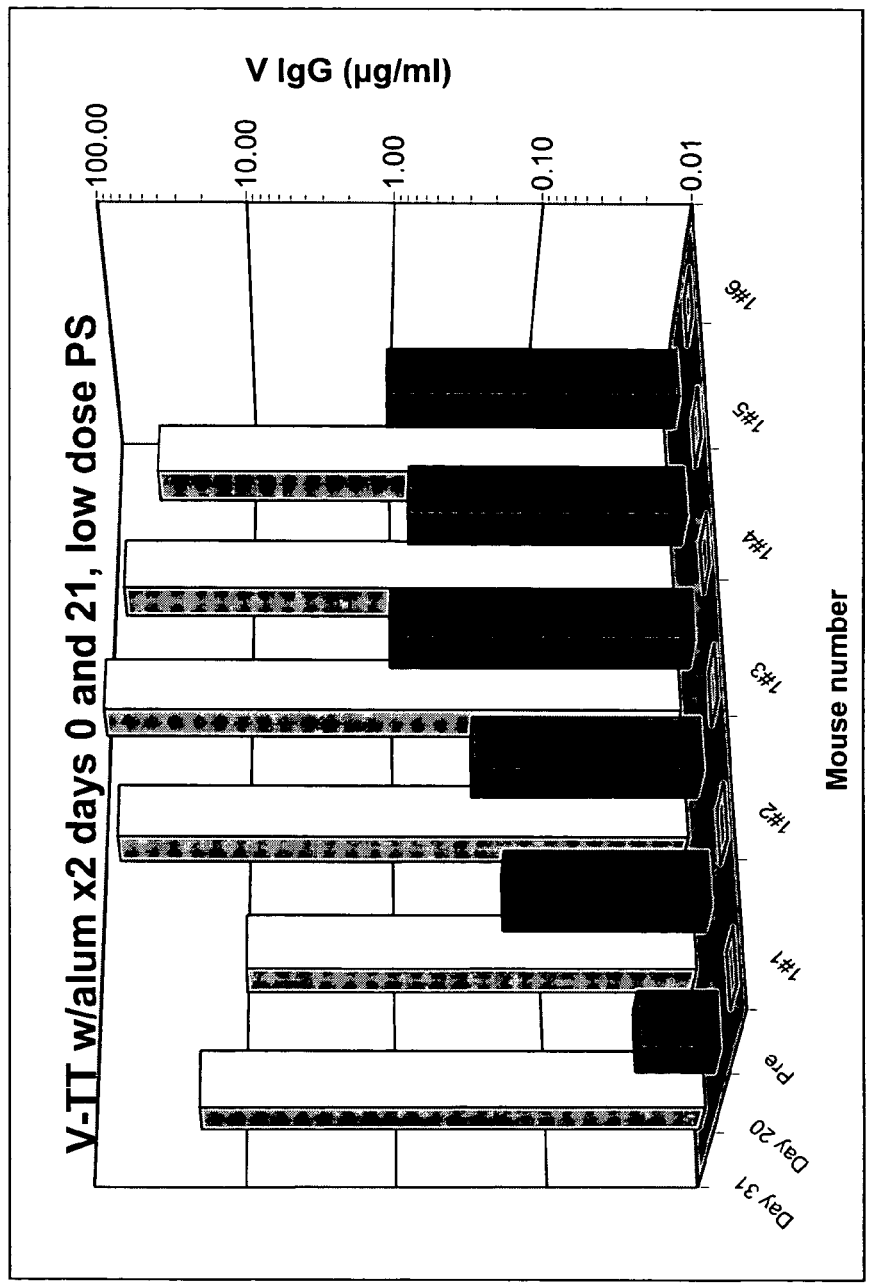

FIG. 27B is a graph depicting the levels of V-specific IgG induced in six different mice immunized with 0.625 µg per dose of a GBS V-TT conjugate vaccine with 0.5 mg of alum per dose. Results for sera obtained prior to immunization, at day 20, and at day 31 are shown.

Figure 27C:
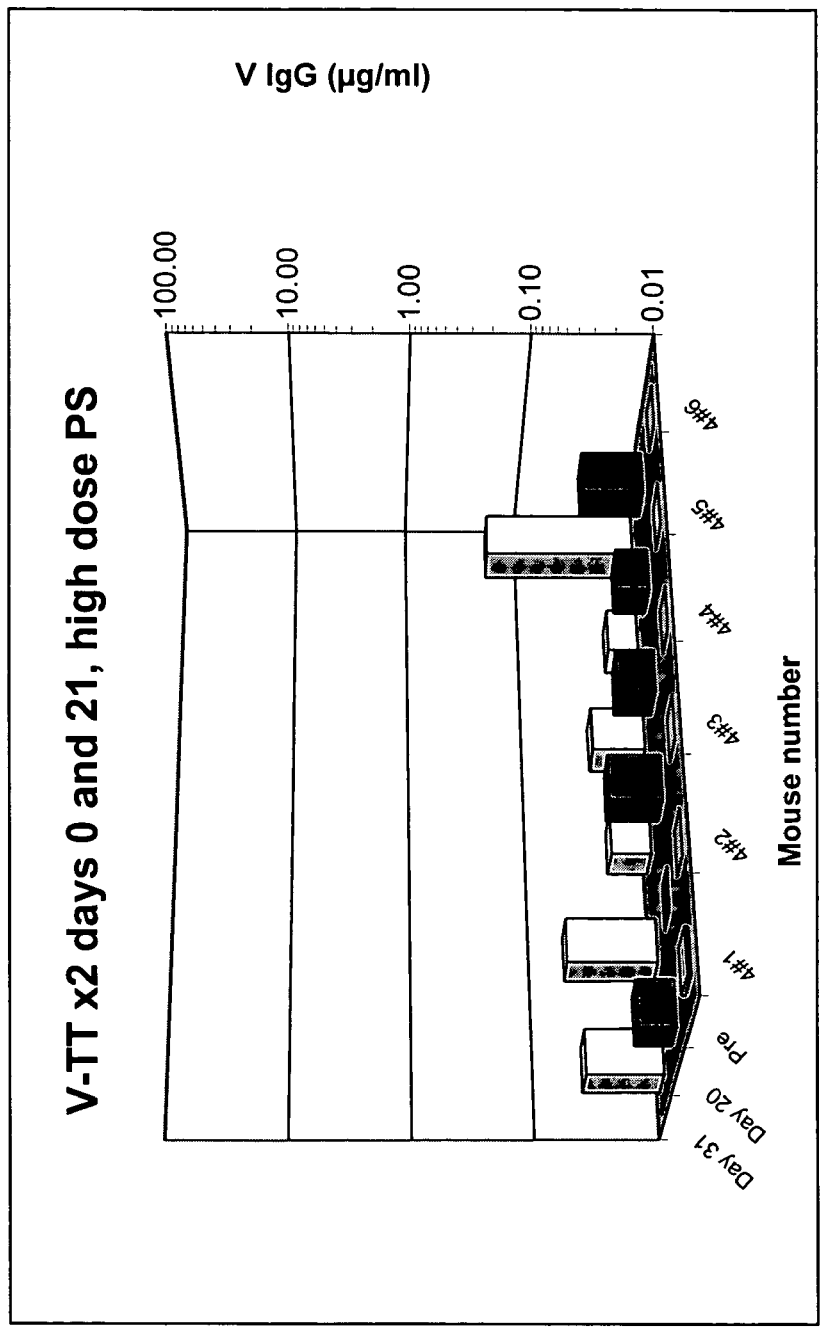

FIG. 27C is a graph depicting the levels of V-specific IgG induced in six different mice immunized with 6.25 µg per dose of a GBS V-TT conjugate vaccine. Results for sera obtained prior to immunization, at day 20, and at day 31 are shown.

Figure 27D:
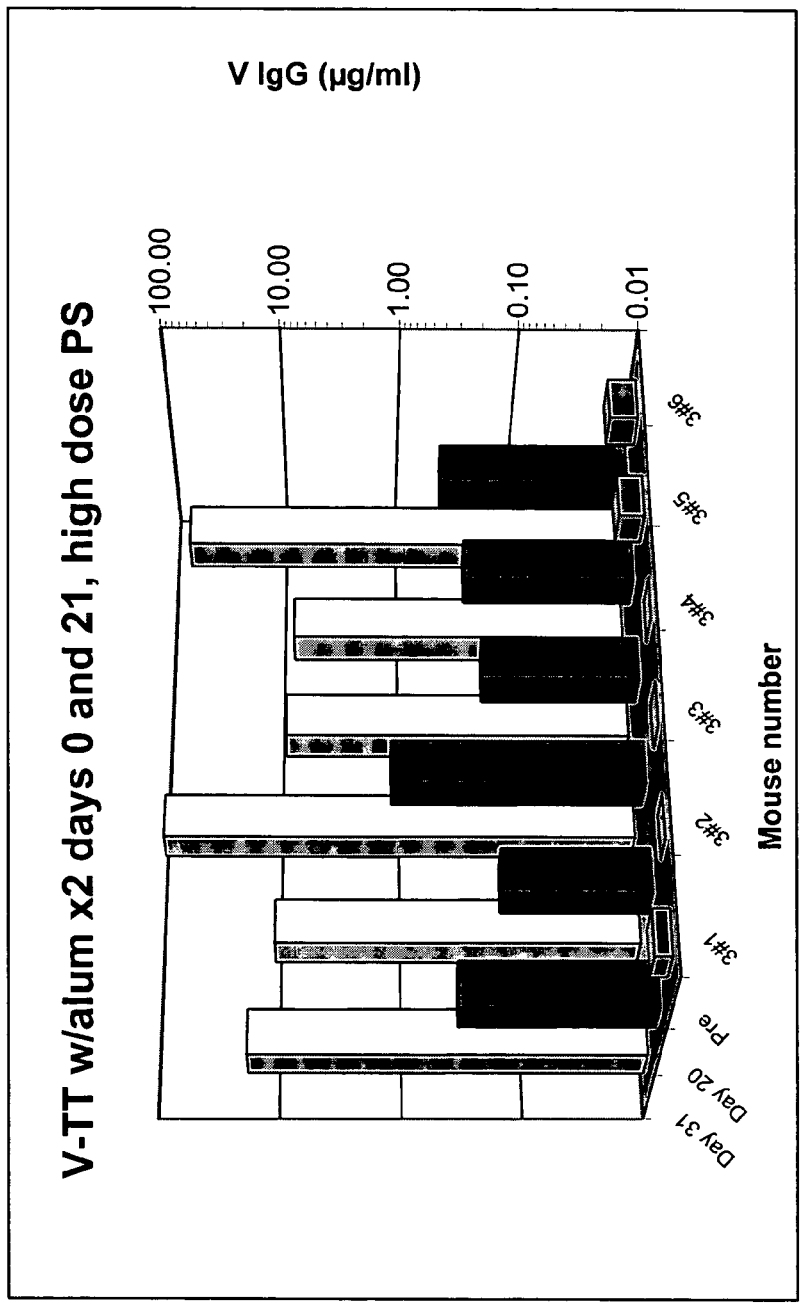

FIG. 27D is a graph depicting the levels of V-specific IgG induced in six different mice immunized with 6.25 µg per dose of a GBS V-TT conjugate vaccine with 0.5 mg of alum per dose. Results for sera obtained prior to immunization, at day 20, and at day 31 are shown.

Like reference symbols in the various drawings indicate like elements.

DETAILED DESCRIPTION

Clinical studies have shown that polysaccharide-protein conjugate vaccines are safe and immunogenic in humans (Baker et al., *J Infect Dis.*, 179:142-150, 1999; Baker et al., *J Infect Dis.*, 182:1129-1138, 2000; Kasper et al., *J Clin Invest.*, 98:2308-2314, 1996). Vaccines that elicit IgG antibodies are preferred because IgG antibodies are long lasting and cross the placenta, thereby providing protection for newborn infants. We have shown that modified forms of bacterial polysaccharides elicit more potent IgG responses than native forms of the polysaccharides. More specifically, we have generated modified forms of GBS V PS which lack one or more sidechain residues and we found that compositions including these modified forms (e.g., polysaccharide-polypeptide conjugates) elicit GBS V-specific IgG antibodies in primates. The modified polysaccharide compositions described herein are particularly useful for eliciting antibody responses in humans. These compositions can provide beneficial responses in subpopulations at highest risk for infection (e.g., in the elderly, and in neonates via maternal transmission of IgG).

Figure 1:
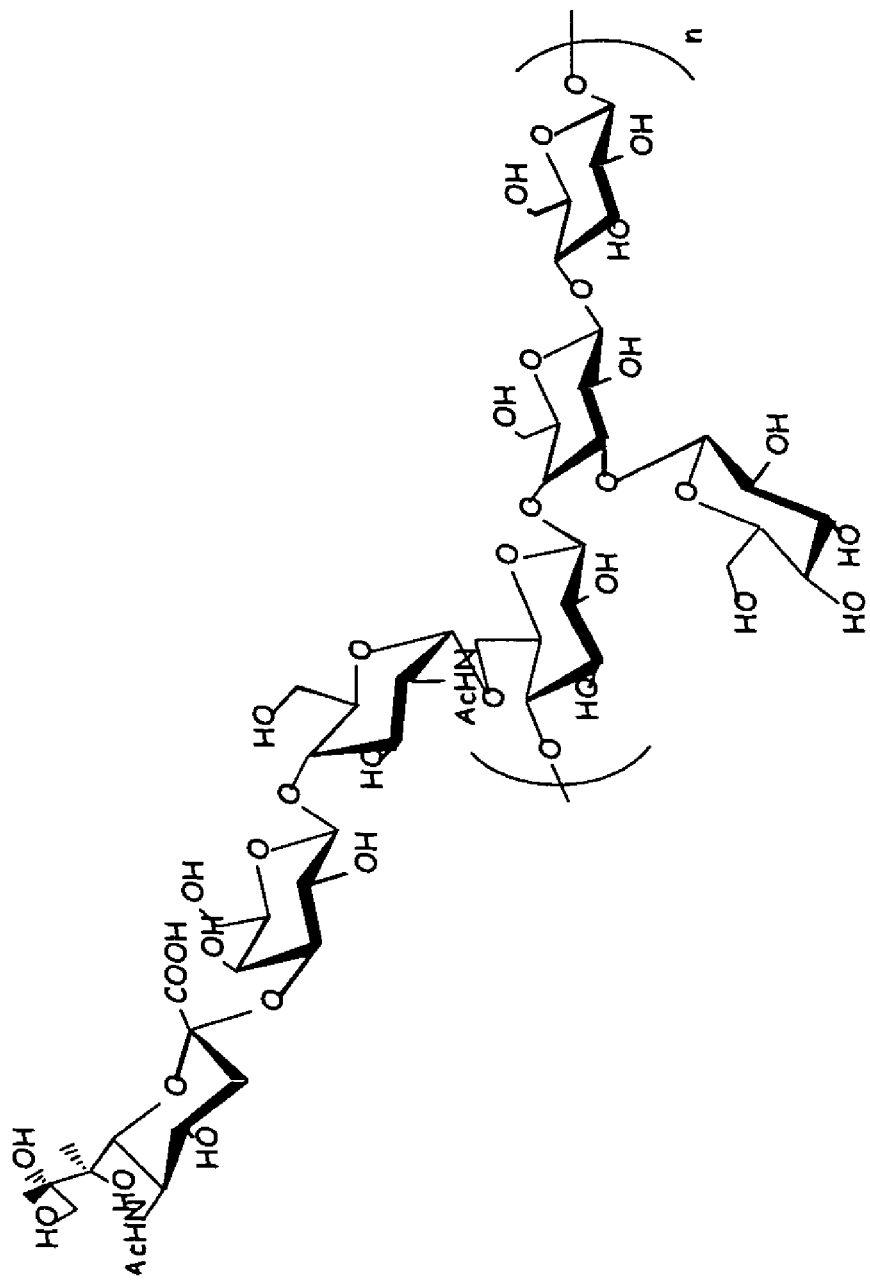
FIG. 1 is a graphic depiction of the structure of the heptasaccharide repeating unit of GBS type V capsular polysaccharide.

GBS Type V Polysaccharides and Modified Forms Thereof. GBS capsular polysaccharides are high molecular weight polymers of repeating units comprising galactose, glucose, N-acetyl glucosamine, and sialic acid residues. The repeating unit of native GBS type V CPS is a heptasaccharide containing a trisaccharide backbone with two distinct side chains, as depicted graphically in FIG. 1 and FIG. 2A (see Wessels et al., *J Biol Chem.*, 266(11):6714-9, 1991). The trisaccharide backbone of GBS V CPS has the following structure:

$$\rightarrow 4)\text{-}\alpha\text{-D-Glcp-}(1\rightarrow 4)\text{-}\beta\text{-D-Galp-}(1\rightarrow 4)\text{-}\beta\text{-D-Glcp-}(1\rightarrow.$$
$$\phantom{xxxxxxx} a \phantom{xxxxxxxxxxxxxx} b \phantom{xxxxxxxxxxxxxx} c$$

(Glcp is glucopyranosyl and Galp is galactopyranosyl). A trisaccharide branch having the following structure is linked to D-Glcp marked "a" through the O-6 of the latter:

α-D-NeupNAc-(2→3)-β-D-Galp(1→4)-β-D-GlcpNAc (1→.

A D-Glcp residue is linked to the D-Galp marked "b" through the O-3 of the latter.

Isolation of Type V Polysaccharides. GBS type V CPS can be prepared from GBS type V bacterial cultures using known methods. For example, to isolate CPS, a GBS type V strain (e.g., CJB111) is grown in continuous culture in a chemically defined medium. Cells are harvested by centrifugation and CPS is removed by base extraction or treatment with the endo-N-acetylmuramidase mutanolysin. Purification of CPS with mutanolysin is described in Deng et al. (*J. Biol. Chem.*, 275(11):7497-7504, 2000). Extracts are treated with RNAse A, DNAse I, RNAse T1, and pronase. A fraction containing CPS is isolated by size-exclusion and ion-exchange chromatography. Methods for preparation of purified GBS V CPS can be performed as described for preparation of GBS III CPS (see, e.g., Wessels et al., *J Clin Invest.*, 86:1428-1433, 1990).

Production of Modified Type V Polysaccharides. GBS polysaccharides can be modified by techniques known in the art. For example, desialylated GBS type V CPS can be prepared by treating purified type V CPS under mildly acidic conditions (e.g., 0.1M sulfuric acid at 80° C. for 60 minutes) or by treatment with neuraminidase. The mixture can be purified by chromatography. Deaminated GBS type V CPS can be prepared by first treating desialylated type V CPS with base to deacetylate the CPS (e.g., 2M NaOH and sodium borohydride, heating to 100° C. for 5 hours, followed by neutralization with acetic acid and lyophilization). Next, the deacetylated CPS is deaminated (e.g., by dissolving in water and aqueous acetic acid, followed by treatment with aqueous sodium nitrite for 1.5 hours at room temperature and purification by ion-exchange chromatography; see Wessels et al., *J Biol Chem.*, 266(11):6714-9, 1991).

In various embodiments, modified polysaccharides are prepared by producing the polysaccharides in a bacteria in which nucleic acid sequences encoding polysaccharide-modifying enzymes have been genetically manipulated (e.g., genes encoding the enzymes have been deleted, rendered non-functional, or are inserted or overexpressed). Genes encoding polysaccharide-modifying enzymes of GBS V are described, e.g., in Tettelin et al., *Proc Natl Acad Sci USA*, 99(19):12391-6, 2002.

A GBS V conjugate can be mixed with one or more conjugates comprising other polysaccharides (e.g., GBS type I, II, III, or IV) to provide a multivalent composition for immunization. Alternatively, multivalent polysaccharide compositions for immunization can be generated by conjugating multiple types of polysaccharides in a single reaction.

Conjugation of Modified Type V Polysaccharides. Modified GBS polysaccharides can be conjugated to carrier moieties using art-known methods. For example, polysaccharides can be oxidized by treatment with periodate (or a related reagent, e.g., paraperiodic acid or potassium metaperiodate) to leave aldehydic termini at sites with vicinal dihydroxy groups. Treated polysaccharides can be reacted with the carrier moiety under conditions that conjugate the components, e.g., using a linking reagent or via direct coupling to the moiety. Conjugation to polypeptide moieties may be carried out, e.g., by reductive amination (see, e.g., Schwartz and Gray, *Arch. Biochem. Biophys.* 181: 542-549, 1977). Briefly, oxidized CPS and the polypeptide moiety are reacted in the presence of cyanoborohydride ions, or another reducing agent which will not reduce the reducing ends of interest nor adversely affect the polypeptide or capsular polysaccharide. Methods for conjugating polysaccharides are also described, e.g., in Wessels et al., *J Clin Invest.*, 86:1428-1433, 1990 and Wang et al., *Vaccine*, 21(11-12):1112-7, 2003.

Suitable carrier moieties are safe for administration to mammals (e.g., young mammals) and are effective immunologically (e.g., they facilitate T cell-dependent antibody responses to the polysaccharide). Exemplary carrier moieties are diphtheria and tetanus toxoids.

In general, any compound can serve as a carrier moiety. Bacterial toxins such as tetanus and diphtheria toxins bind to mammalian cell surfaces, thereby permitting the polysaccharide to which they are conjugated to more effectively initiate immune responses. Another exemplary carrier polypeptide, CRM197, is a diphtheria toxin containing a single amino acid change from native diphtheria toxin and which is immunologically indistinguishable from native diphtheria toxin. A culture of Corynebacterium diphtheria strain C7 (β197), which produces CRM197 is available from the American Type Culture Collection, 10801 University Boulevard, Manassas, Va. 20110-2204, under accession number ATCC 53281.

Other bacterial polypeptides can be used as carrier moieties. In various embodiments, secreted or surface-expressed bacterial polypeptides are used (e.g., secreted or surface-expressed polypeptides of streptococcal bacteria such as GBS bacteria). For example, modified GBS V polysaccharides can be conjugated to GBS C protein alpha polypeptides or antigenic fragments thereof. GBS C protein alpha is a surface-associated polypeptide which contains up to nine tandemly repeated units of 82 amino acids (Michel et al., *Proc Natl Acad Sci USA* 89: 10060-10064, 1992). Bacterial C protein alpha polypeptides and methods of using them for vaccination are described in U.S. Pat. Nos. 5,968,521, 5,908,629, 5,858,362, 5,847,081, 5,843,461, 5,843,444, 5,820,860, and 5,648,241. An antigenic fragment can include one or more of the tandemly repeated units of 82 amino acids. GBS C protein beta or epsilon polypeptides (or antigenic fragments thereof) may be conjugated to modified GBS V polysaccharides. The GBS C protein beta, C protein epsilon, R protein (also known as Rib and R4), Alpha-like proteins (Alps), surface protein of group B *streptococcus* 1 (spb1), spb2, and Lmb (laminin binding protein) can also be used as carrier proteins (Heden et al., *Eur J Immunol.*, 21(6):1481-90, 1991; Michel et al., *Infect Immun.*, 1991 June; 59(6):2023-8; Larsson et al., *Infect Immun.*, 64(9):3518-23, 1996; Wastfelt et al., *J Biol Chem.*, 271(31):18892-7, 1996; Ferrieri, P., *Rev. Infect. Dis.*, 10(Suppl. 2):S363-S366, 1988; Kong et al., *J. Clin. Microbiol.*, 40:620-626, 2002; Lachenauer et al., *Proc Natl Acad Sci USA*, 97:9630-9635, 2000; Spellberg et al., *Infect Immun.*, 67(2):871-8, 1999; Adderson et al., *Infect Immun.*, 71(12):6857-63, 2003). A bacterial C5a peptidase or an antigenic fragment thereof (e.g, a streptococcal C5a peptidase, e.g., as described in U.S. Pat. No. 6,355,255) can also be used for conjugation to the modified polysaccharides described herein. Streptococcal matrix adhesion (Ema) polypeptides or antigenic fragments thereof (described in U.S. Pat. Pub. No. 20040071729) may also be used for conjugation to polysaccharides. GBS polysaccharides may be conjugated to more than one polypeptide. For example, a modified GBS polysaccharide may be coupled to two, three, four, or five different bacterial polypeptides.

Polysaccharide compositions can be formulated with adjuvants. Adjuvants may enhance a mammal's immune response to the polysaccharide, e.g., to enhance antibody production and/or to induce an immune response with lower doses of polysaccharide. Adjuvants include: water emulsions (e.g., complete and incomplete Freund's adjuvant); oil; iron oxide; sodium alginate; aluminum hydroxide, aluminum and calcium salts (i.e., alum); unmethylated CpG motifs; glucan; dextran sulfate; bacterial extracts (e.g., mycobacterial extracts); QS-21 (Aquila Biopharmaccuticals, Inc., Framingham, Mass.); MPL™ (3-O-deacylated monophosphoryl lipid A; Corixa, Hamilton, Mont.); 529 (an amino alkyl glucosamine phosphate compound, Corixa, Hamilton, Mont.), N-acetyl-muramyl-L-theron-yl-D-isoglutamine (thr-MDP); N-acetyl-nor-muramyl-L-alanyl-D-isoglutamine (CGP 11637, referred to as nor-MDP); and N-acetylmuramyl-L-alanyl-D-isoglutam-inyl-L-alanine-2-(1'-2'-dipalmitoyl-sn-glycero-3-hydroxyphos-phoryloxy-eth-ylamine) (CGP 19835A, referred to as MTP-PE). Polypeptide adjuvants such as IL-12 (Genetics Institute, Cambridge, Mass.) and GM-CSF (Immunex Corp., Seattle, Wash.) may also be used to enhance the immune response to polysaccharide compositions.

Administration of polysaccharide compositions. Modified polysaccharides and polysaccharide conjugates can be formulated in a suitable carrier media for administration to a subject (e.g., sodium phosphate-buffered saline (pH 7.4) of 0.125M aluminum phosphate gel suspended in sodium phosphate-buffered saline at pH 6 or another conventional media). Suitable pharmaceutical carriers are known in the art.

Compositions for administration to a subject can contain from about 0.1 to about 500 µg of a polysaccharide composition, e.g., about 10 to 50 µg, and can elicit effective levels of antibody against the capsular polysaccharide in mammals. The exact dosage can be determined by routine dose/response experimentation.

Polysaccharide conjugate compositions can be administered as a single immunization or in a series, e.g., two, three or four doses at 1 month, 2 month, 3 month, or longer intervals. A booster may be given one year, two years, or more after the initial immunization or primary series of immunizations. An exemplary immunization schedule for pregnant women is a single dose given in the second or early third trimester. For immunization of non-pregnant adults, a single dose can be used. The requirement for subsequent booster doses in adults can be based on the immunogenicity of the polysaccharide composition and ongoing surveillance of efficacy of the vaccine in eliciting an immune response.

EXAMPLES

Example 1

Characterization of GBS V-specific Antibodies in Human Sera

Unconjugated polysaccharide vaccines or glycoconjugate vaccines to type Ia, type Ib, and type III group B *Streptococcus* (GBS) elicit primarily IgG antibodies in humans. In contrast, type V GBS induces primarily IgM and IgA antibodies. Neither IgM nor IgA isotypes cross the placenta to protect neonates against invasive disease.

Types Ia, Ib, and III GBS polysaccharides, which induce strong IgG responses, are polymers of repeating units with two or three sugars in the backbone and a three-sugar sidechain with a sialic acid residue at the end of the sidechain. Type V polysaccharides, which induce low levels of IgG antibodies, are polymers of a repeat unit containing a three-sugar backbone with two sidechains, one of which is a glucose residue directly linked to the backbone, the other of which is a three-sugar side-chain, the terminal residue of which is a sialic acid.

Chemically modified type V polysaccharides were prepared to examine epitope presentation and determine optimal epitopes for inducing an IgG response in humans. Competitive enzyme-linked immunosorbent assays (competitive ELISA) were used to determine reactivity to GBS V PS of antibodies in the IgG fraction of a serum pool from 5 human volunteers immunized with GBS V-tetanus toxoid conjugate (GBS V-TT) in the presence of various modified forms of GBS V PS. In these assays, the modified GBS V PS were referred to as "inhibitors", i.e., inhibitors of binding to native GBS V PS.

To detect GBS PS-specific antibodies, IgG fractions of antisera were allowed to bind to native GBS V PS-HSA coated onto plastic 96 well plates (ELISA plates) in the presence of various amounts of free polysaccharides in solution. In these and all ELISA experiments reported in the following examples, the native polysaccharide used as a coating antigen was a form conjugated to HSA. Methods other than ELISA can be used for detection of PS-specific antibodies, e.g., other art-recognized methods for evaluating antibody-antigen interactions (in solution or on a solid phase).

The results of binding of the IgG fractions to native GBS V PS-HSA are shown in FIG. 3. The concentration of inhibitors is depicted along the X-axis on a logarithmic scale in µg/ml and the percentage inhibition of binding of the antibodies to the PS bound to the ELISA plates is depicted along the Y-axis on a linear scale. Polysaccharides tested for inhibition were: (1) native type V polysaccharide consisting of a polymer of approximately 200 repeat units (filled triangles); (2) chemically modified type V polysaccharide representing reduced size type V oligosaccharide (OS) obtained by ozone treatment of the PS (open triangles); (3) full length desialylated GBS V PS (filled circles); (4) deaminated GBS V PS which contains the type V backbone with the single-sugar side-chain (filled squares); (5) GBS V PS without the single sugar side-chain (which is identical to the structure of GBS VII PS)(diamonds); and (6) GBS IV PS (open circles).

All of the vaccine-induced antibodies recognized the deaminated (filled squares) and the desialylated type V PS (filled circles) as shown by the overlapping inhibition curves for these chemically modified polysaccharides. Antibody binding to native type V PS was inhibited by native type V PS, as expected (filled triangles). The modified type V PS lacking the single-sugar sidechain (diamonds) did not inhibit binding. Thus, this sidechain is a critical dominant epitope for the antibodies. These data also show that the dominant epitope is dependent on the size of the type V polymer, as longer native type V PS (204 kDa, filled triangles) was a much better inhibitor than a shorter version of native type V PS (7.8 kDa, open triangles).

The $IC_{50}$ of each polysaccharide is shown in Table 1.

TABLE 1

$IC_{50}$ of Polysaccharides for Human V-TT Induced V-specific IgG Fraction Antisera

| Inhibitor | $IC_{50}$ (µg/ml) |
|---|---|
| Type V PS | 0.3 |
| Type VII PS | No inhibition |
| Type IV PS | >270 |
| Desialylated Type V PS | 0.14 |
| Deaminated Type V PS | 0.09 |

Figure 4:
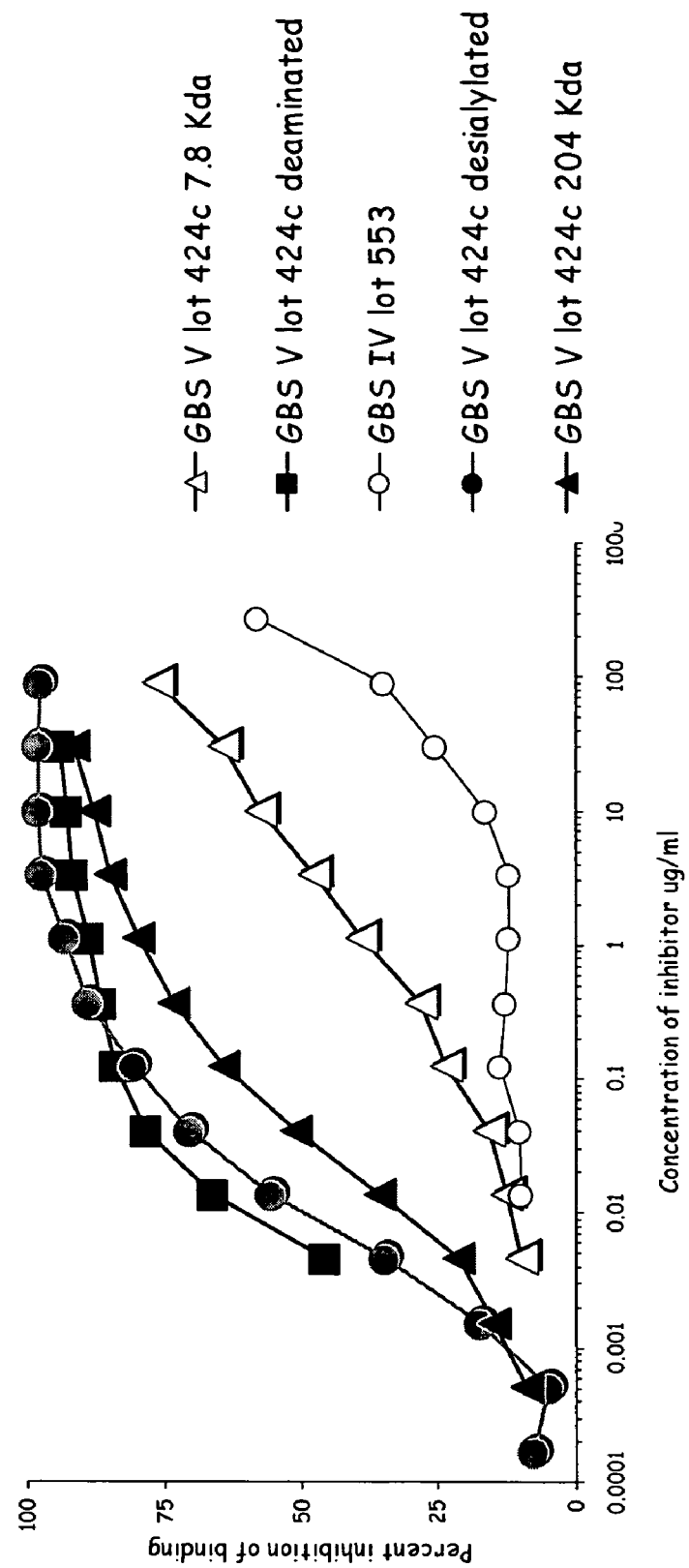
FIG. 4 is a graph depicting the inhibition of binding by IgM fraction of human serum of subjects immunized with a GBS type V polysaccharide-tetanus toxoid (GBS V-TT) conjugate vaccine to native GBS type V in the presence of various forms of GBS type V PS.

A similar pattern of inhibition by GBS polysaccharides was observed for the IgM fraction of vaccine-induced GBS V-specific antibodies in the human serum pool for GBS V, in which desialylated, deaminated, and longer native type V PS (204 kDa) inhibited binding more potently than shorter native type V PS (7.8 kDa) and type IV PS (FIG. 4). Thus, the single-sugar side chain is also a dominant epitope for recognition by IgM antibodies. The $IC_{50}$ of each polysaccharide is shown in Table 2. Similar results were obtained for the IgG and the IgM fractions of vaccine-induced human sera from a total of 10 volunteers tested so far.

TABLE 2

$IC_{50}$ of Polysaccharides for Human V-TT Induced V-specific IgM Fraction Antisera

| Inhibitor | $IC_{50}$ (µg/ml) |
|---|---|
| Type V PS | 0.13 |
| Type VII PS | Not determined |
| Type IV PS | 190 |
| Desialylated Type V PS | 0.013 |
| Deaminated Type V PS | 0.005 |

Example 2

Function of Type V-Specific Antibodies

Next, the function of antibodies induced by the GBS V-TT glycoconjugate was examined. In humans, GBS are cleared by a process called antibody-dependent complement-mediated opsonophagocytic killing. In the case of PS-based vaccines, PS-specific vaccine-induced antibodies recognize epitopes or binding sites on the capsular polysaccharide of the GBS bacteria. Antibody binding leads to complement activation and deposition of activated complement components on the bacteria. The antibodies and complement components on the opsonized bacteria are recognized by professional phagocytes, e.g., via Fc Receptors and complement receptors, and are taken up in a process called opsonophagocytosis. GBS that are engulfed by phagocytes such as polymorphonuclear leukocytes (PMNL) are killed by various mechanisms such as oxidative burst. FIG. 5 shows data from an in vitro assay that measures antibodies' ability to promote opsonophagocytic killing by PMNL in the presence of complement. In this assay, antibodies, complement, bacteria and PMNL are incubated at body temperature. The killing of the bacteria after 60 minutes of incubation is recorded as loss of live bacteria from the reaction mixture. GBS V-specific antibodies are able to mediate killing of the GBS bacteria. As shown in FIG. 5, both the IgG antibody fraction (black bars) and the IgM antibody fraction (striped bars) of the standard human serum reference pool promote killing of GBS. A concentration of 3 µg/ml of GBS type V-specific IgG was required for killing more than 90% of bacteria in the reaction mixture, whereas 0.1 µg/ml of type V-specific IgM promoted killing of more than 90% of the bacteria. Thus the IgM fraction is more efficient in promoting killing of the bacteria. Whole serum of immunized humans (white bars), and non-immune human serum (gray bars) were included in each assay as controls.

Figure 6:
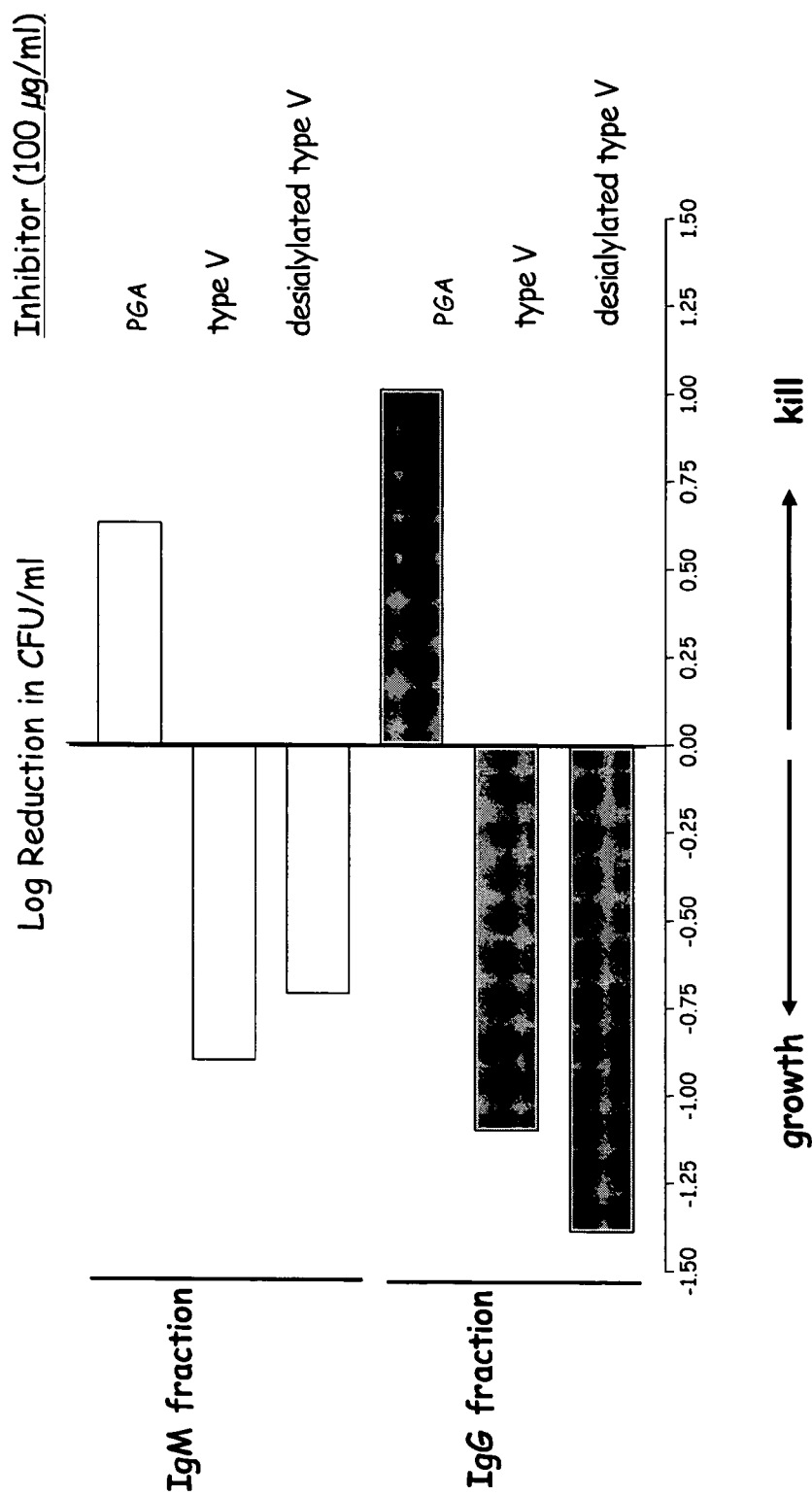
FIG. 6 is a bar graph depicting opsonophagocytic killing and growth of GBS type V bacteria by GBS type V-TT-induced human antisera (IgM fraction, white bars; IgG fraction, gray bars) in the presence of PGA, type V, and desialylated type V polysaccharides).

Next, the IgG fraction and the IgM fraction of human GBS V-TT induced antibodies were tested for killing in the presence of type V PS, desialylated type V PS, and an irrelevant polysaccharide, polygalacturonic acid (PGA). Antibodies were tested at concentrations that give ~90% reduction of live bacteria (1 log killing). Strain CJB 111 of GBS V was used for this experiment. As shown in FIG. 6, desialylated type V and native type V PS in the reaction mixture completely abolished the killing of GBS by PMNL in the presence of V-specific IgM (white bars) as well as V-specific IgG antibodies (gray bars) as demonstrated by growth (bars extending to the left of 0.00 on the X-axis), and lack of killing (bars extending to the right of 0.00 on the X-axis), of the bacteria. PGA did not have any effect on the stimulation of opsonophagocytosis of the vaccine-induced V-specific IgM and V-specific IgG antibodies.

Example 3

Characterization of Murine GBS V-Specific Antibodies

Sera from mice immunized with GBS III-TT and GBS V-TT glycoconjugate vaccines were characterized. It was found that one dose of both the GBS III-TT and GBS V-TT glycoconjugate vaccines induced IgM antibodies and low levels of PS-specific IgG antibodies (data not shown). Repeated immunizations with the either of the glycoconjugate vaccines resulted in comparable increases in isotype switching to IgG of PS-specific antibodies. GBS V-specific responses were more rapid and robust after second and third immunizations indicating induction of immunologic memory to the antigen (data not shown).

A GBS V-specific murine monoclonal antibody was tested in the competitive ELISA assay described in Example 1. In contrast to human IgG, murine IgG recognize the native capsular polysaccharide and not the desialylated polysaccharide (FIG. 7). The graph in FIG. 7 shows that desialylated GBS V PS binds much more weakly to the murine GBS V-induced IgG as compared to the native polysaccharide. The deaminated GBS V PS, which is the dominant epitope in humans, were not recognized by the murine antibodies at all. The $IC_{50}$ of each polysaccharide was calculated and is shown in Table 3. Similar results have been obtained for all murine monoclonal and polyclonal sera tested.

TABLE 3

$IC_{50}$ of Polysaccharides for Murine V-TT Induced V-specific IgG Fraction Antisera

| Inhibitor | $IC_{50}$ (µg/ml) |
|---|---|
| Type V PS | 0.04 |
| Type VII PS | >810 |
| Type IV PS | No inhibition |
| Desialylated Type V PS | 0.7 |
| Deaminated Type V PS | >10 |

These data show that the immune response of mice to GBS type III and type V is different from the human immune response with respect to isotype switching, dominant B-cell epitopes, and functional epitopes.

Example 4

GBS Type III Polysaccharide-Specific Responses in Rhesus Macaques

A group of three young non-pregnant female rhesus macaques (*Macaca mulatta*) were immunized twice with GBS type III-TT (50 µg PS, intramuscularly) with 8 weeks between immunizations. Sera were obtained before immunization and weekly after immunizations for evaluating levels, isotypes, and functions of vaccine-induced PS-specific antibodies and carrier-specific (i.e., tetanus toxoid-specific) antibodies. The vaccines were well-tolerated by the macaques.

Figure 8:
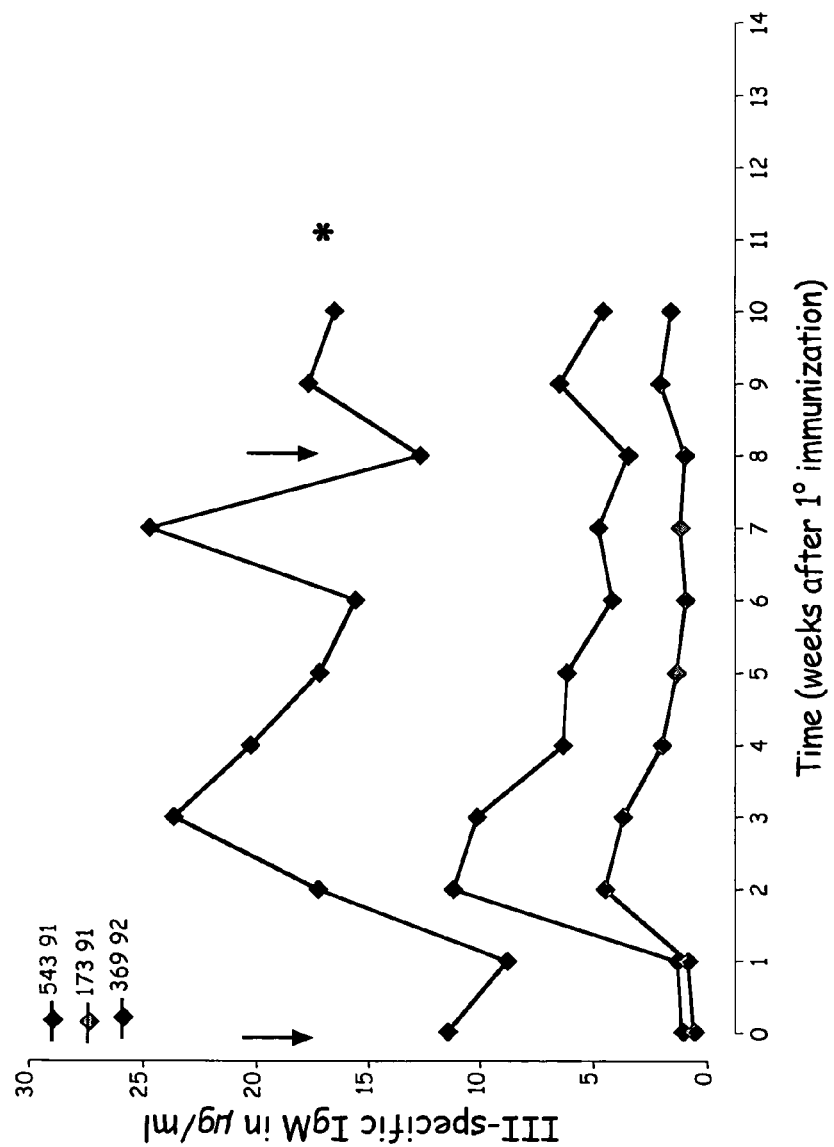
FIG. 8 is a graph depicting GBS III-specific IgM responses to a GBS III-TT vaccine in rhesus macaques. Each line corresponds to values obtained for sera from an individual monkey.

IgM, IgA, and IgG antibody responses to the type III PS were examined. FIG. 8 depicts GBS III-specific IgM response before and after two immunizations with the GBS III-TT glycoconjugate vaccine in three rhesus macaque monkeys, with each line representing the levels of antibody from an individual monkey. The time in weeks after the first immunization is shown on the X-axis and the levels of type III-specific IgM antibodies in µg/ml are shown on the Y-axis. The immunizations are indicated by the black arrows.

Two of the three monkeys immunized with GBS III-TT did not have pre-existing antibodies to GBS III before the first immunization. GBS III-specific IgM antibodies were detected two weeks after the first immunization in these two monkeys. The levels of GBS III-specific IgM peaked after two weeks, and there was no booster effect of a second dose of the GBS III-TT vaccine.

One of the three monkeys (monkey # 369 92, top line) had pre-existing IgM antibodies to the polysaccharide vaccine antigen before the immunizations. However, these antibodies were not specific for the GBS III PS antigen because addition of a huge access of purified GBS III PS to the reaction mixture had no effect on the binding of the antibodies to the ELISA plates. Due to the high levels of pre-existing natural antibodies that cross-reacted with GBS III PS, we disregarded the values obtained after vaccination in further analyses.

Figure 9:
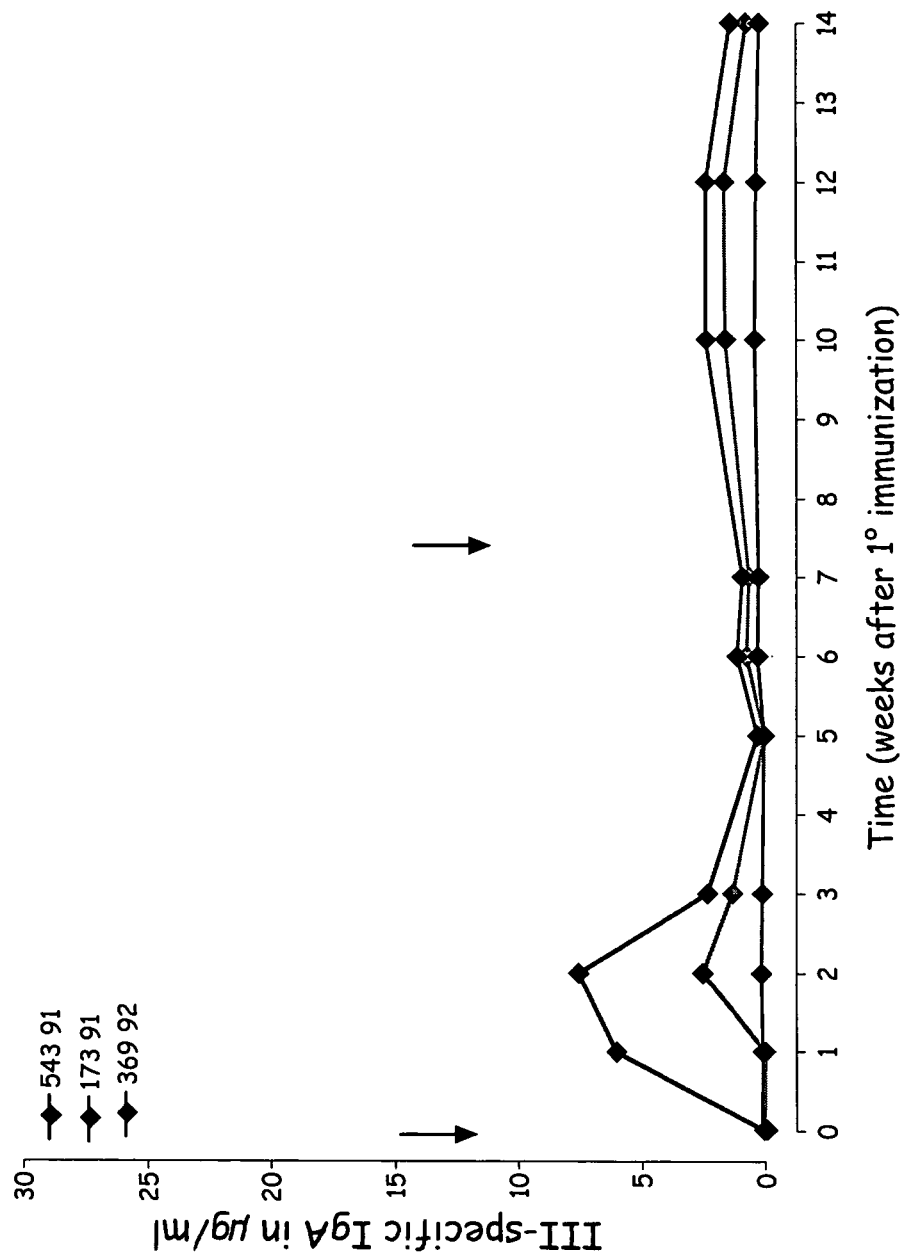
FIG. 9 is a graph depicting GBS III-specific IgA responses to a GBS III-TT vaccine in rhesus macaques. Each line corresponds to values obtained for sera from an individual monkey. The immunizations are indicated by the black arrows.

IgA responses to the GBS III PS are shown in FIG. 9. Two of the three monkeys showed a low level of IgA isotype switched antibodies to type III PS. The third monkey (monkey # 369 92, which had non-specific GBS III-reacting IgM antibodies) did not demonstrate any isotype switching to GBS III-specific IgA antibodies.

Figure 10:
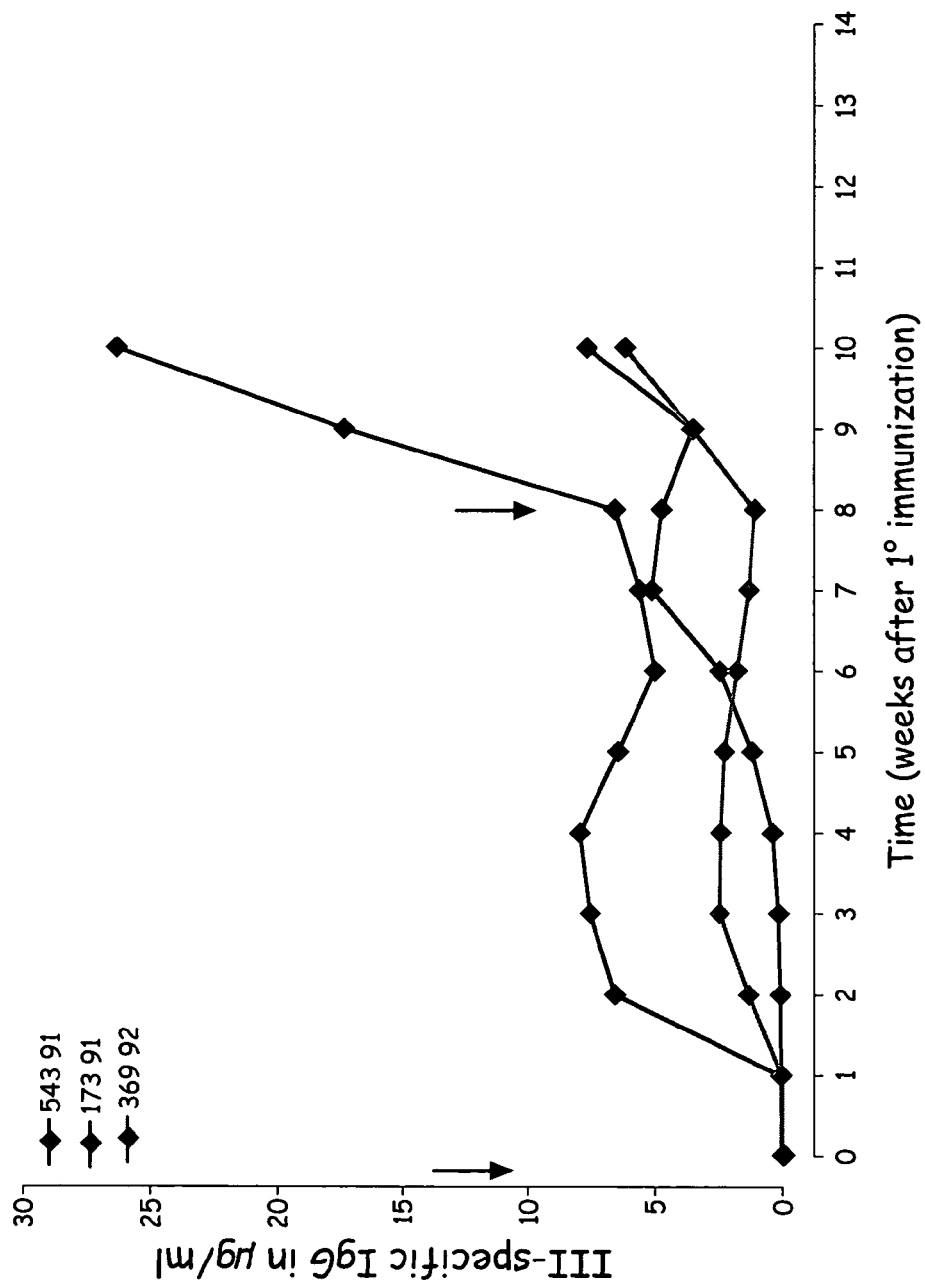
FIG. 10 is a graph depicting GBS III-specific IgG responses to a GBS III-TT vaccine in rhesus macaques. Each line corresponds to values obtained for sera from an individual monkey.

The IgG antibody responses of each monkey are shown in FIG. 10. Two of the three animals responded with significant isotype switching to GBS III PS-specific IgG after the first dose of the GBS III-TT conjugate vaccine. Furthermore, the vaccine primed for GBS III-specific immunologic memory that was recalled by the second or "booster" immunization with GBS III-TT glycoconjugate vaccine resulting in (1) an accelerated antibody response, and (2) a substantial increase in the levels of GBS III-specific IgG antibodies.

In conclusion, these data show that the antibody response to the GBS III-TT glycoconjugate vaccine in rhesus macaques includes substantial isotype switching to IgG, similar to what has been observed in humans.

Example 5

GBS V Polysaccharide-Specific Responses in Rhesus Macaques

Three young non-pregnant female rhesus macaques were immunized twice with GBS V-TT (50 μg PS, intramuscularly) with 8 weeks between immunizations. Sera were obtained before immunization and weekly after immunizations to assess levels, isotypes and functions of vaccine-induced PS-specific antibodies and carrier-specific (i.e., tetanus toxoid-specific) antibodies. The GBS V-TT vaccines were well-tolerated by the macaques.

Figure 11:
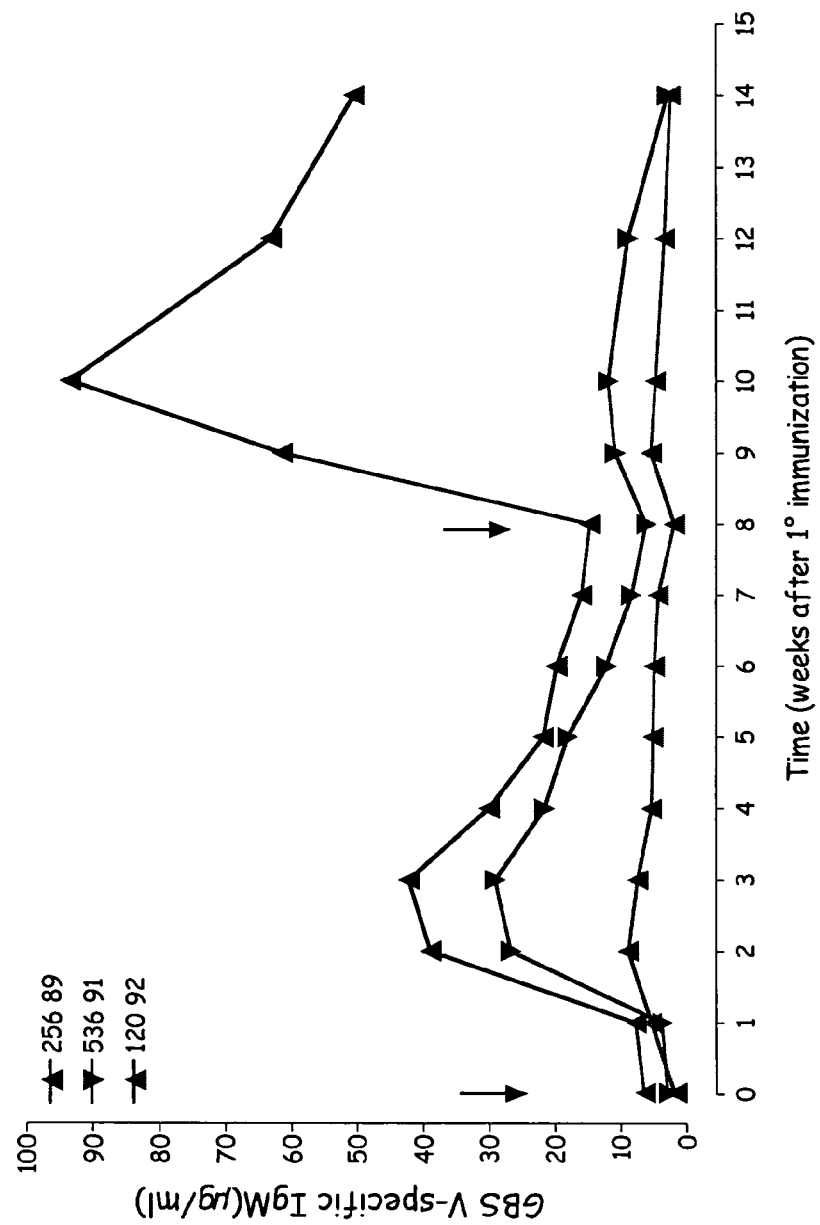
FIG. 11 is a graph depicting GBS V-specific IgM responses to a GBS V-TT vaccine in rhesus macaques. Each line corresponds to values obtained for sera from an individual monkey.

Type V-specific IgM antibody responses before and after two immunizations with GBS V-TT glycoconjugate vaccine in three rhesus macaque monkeys are depicted in FIG. 11. Each line represents the response in an individual monkey. None of the three monkeys immunized with GBS V-TT had pre-existing IgM antibodies to GBS V PS before the immunizations. All three animals had a substantial GBS V IgM response after the first dose of GBS V-TT vaccine, with peak levels exhibited at 2-3 weeks after the immunization. A further increase in type V-specific IgM levels was elicited in one of the three monkeys after the second immunization with GBS V-TT, with a peak level of type V-specific IgM of 95 μg/ml.

Figure 12:
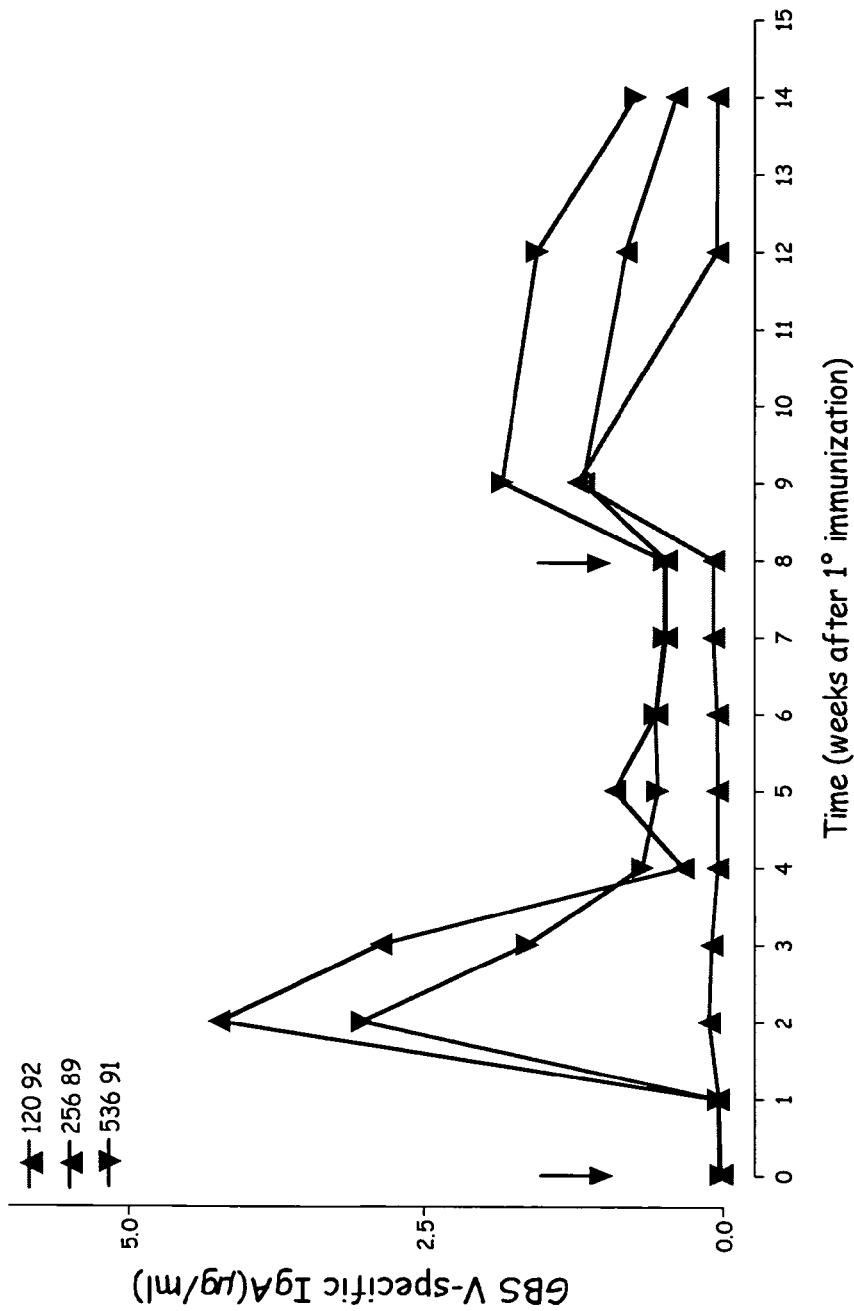
FIG. 12 is a graph depicting GBS V-specific IgA responses to a GBS V-TT vaccine in rhesus macaques. Each line corresponds to values obtained for sera from an individual monkey.

One of the three monkeys had low levels of IgA isotype switched antibodies to GBS V in their serum after the primary immunization (FIG. 12). Low levels of GBS V switched IgA antibodies were observed in all monkeys after the second immunization.

Figure 13:
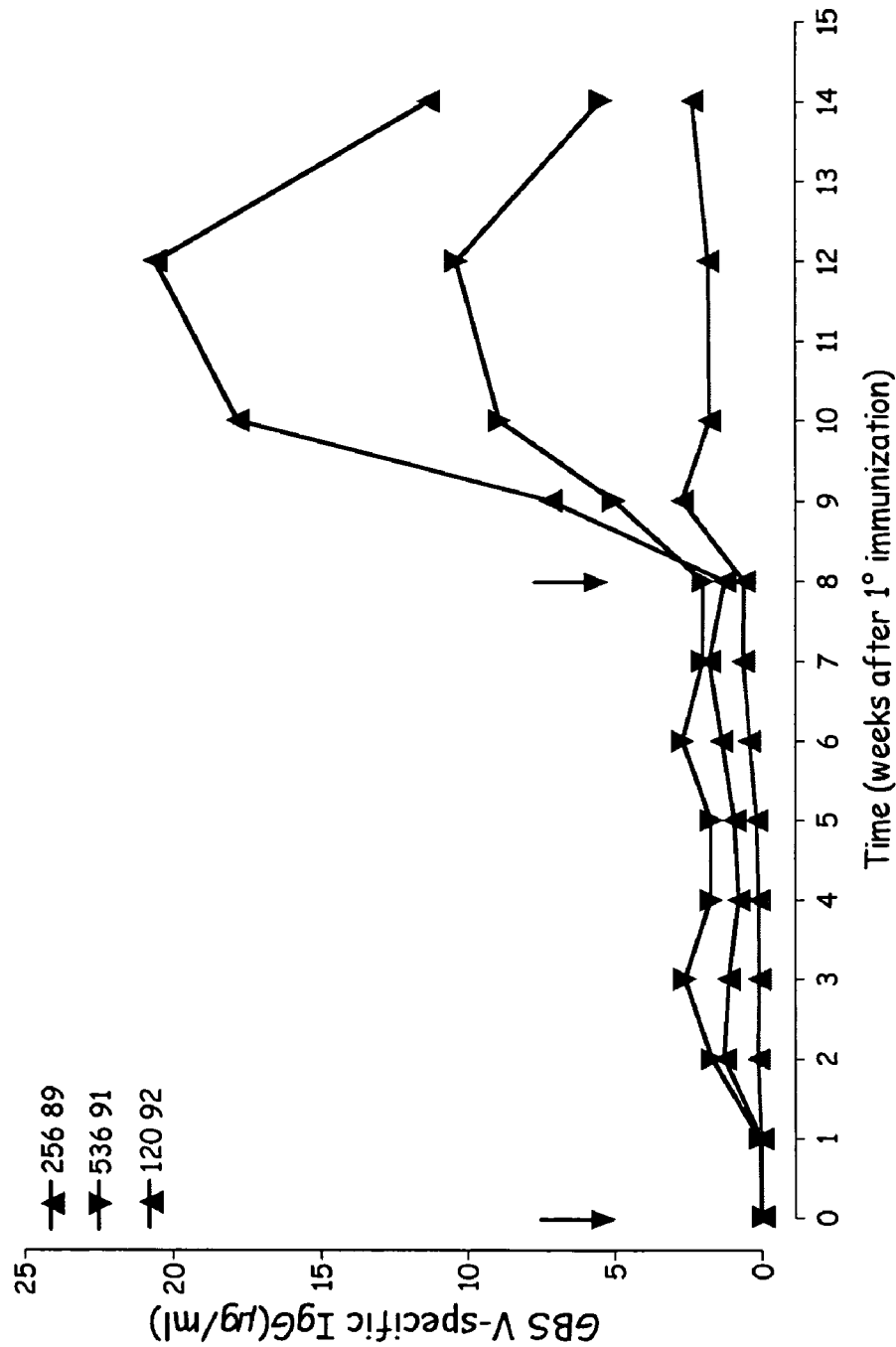
FIG. 13 is a graph depicting GBS V-specific IgG responses to a GBS V-TT vaccine in rhesus macaques. Each line corresponds to values obtained for sera from an individual monkey.

None of the three monkeys immunized with GBS V-TT had pre-existing IgG antibodies to type VPS before the immunizations. The level of IgG-switched PS-specific antibodies was very low after the first immunization, but a significant IgG response was observed after the second vaccination with GBS V-TT (FIG. 13). These data show that isotype response pattern to GBS V-TT glycoconjugate vaccine in rhesus macaques with (1) a substantial IgM response and (2) minimal IgG switching in response to one dose of GBS V-TT is similar to the response in observed in humans.

Levels of isotype-switched GBS V-specific antibodies in humans (hu) and macaques (primates) after primary and secondary immunizations with a GBS V-TT glycoconjugate vaccine were compared (FIG. 14). One dose of the GBS V-TT glycoconjugate vaccine induced very low levels of isotype switching to IgG in both humans and non-human primates. The median percentage of type V-specific IgG switched antibodies was 5% and 12% in humans and primates, respectively. A second dose of the GBS V-TT stimulated higher levels of isotype switching to IgG in both humans and non-human primates. However, the majority of the V-specific antibodies were of the IgM isotype in both species, even after the booster vaccination.

Figure 15:
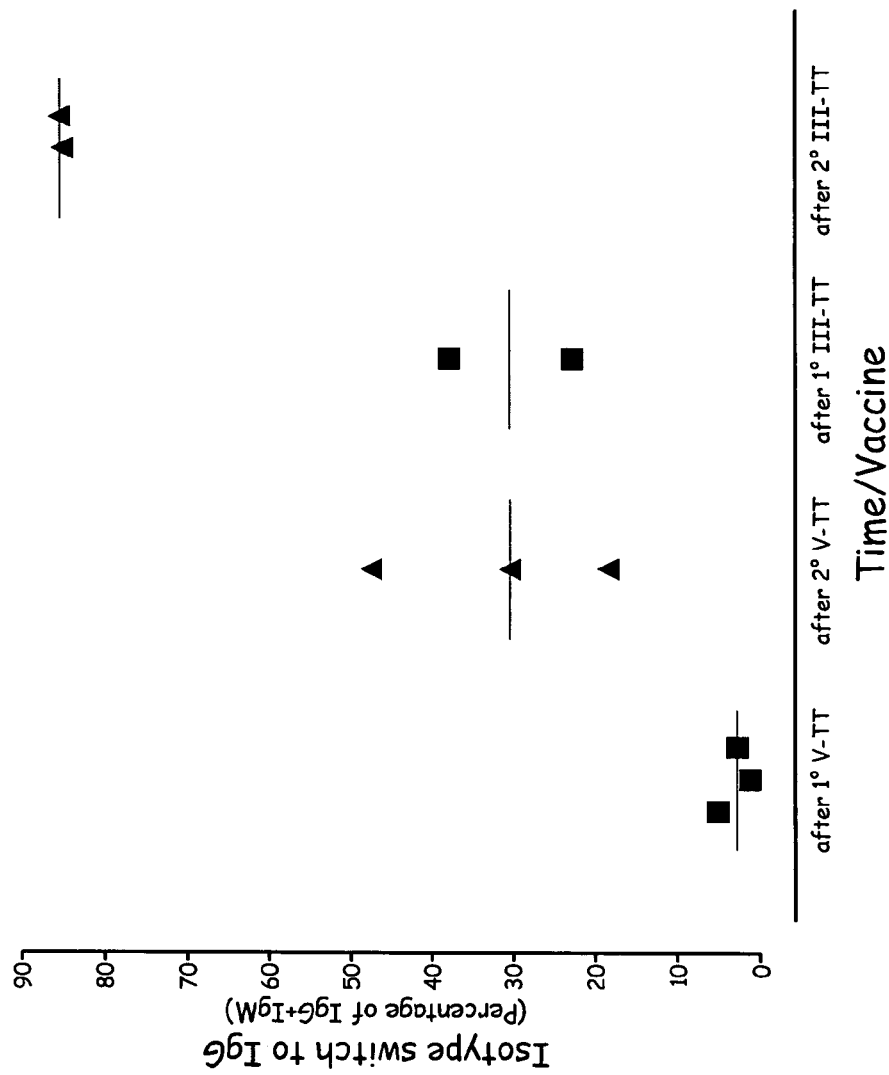
FIG. 15 is a graph depicting levels of isotype-switched GBS III- and GBS V-specific antibodies induced in rhesus macaques after primary and secondary immunization with GBS-TT glycoconjugates vaccines.

Levels of isotype-switched antibodies induced by the Type III-TT and Type V-TT vaccines in macaques were compared (FIG. 15), revealing substantial differences in the isotype switching of the PS-specific antibodies for the two different GBS glycoconjugate vaccines. The GBS V-TT vaccine induced low levels of isotype switching to IgG in macaques, while the GBS type III-TT vaccines induced substantial isotype switching to IgG.

Example 6

Specificity of GBS Type III-Induced IgG Antibodies in Rhesus Macagues

The B-cell epitopes recognized by GBS III-TT vaccine-induced antibodies in macaques were examined by competitive ELISA. The IgG fraction of vaccine-induced antibodies from one monkey immunized with GBS III-TT was allowed to bind to native GBS III CPS coated onto plastic 96-well plates in the presence of various amounts of free polysaccharides or proteins in solution. The results of binding are plotted in FIG. 16. The amount of inhibitors (μg/ml) is shown along the X-axis on a logarithmic scale. The percentage inhibition of antibody binding to the polysaccharides bound to the ELISA plates is shown along the Y-axis on a linear scale. Polysaccharides tested for inhibition were: (1) native GBS III PS consisting of a polymer of approximately 150 repeat units (filled circles); (2) chemically modified GBS III PS representing reduced size type III oligosaccharide (OS) obtained by ozone treatment of the PS (open triangles); (3) full length Pneumococcal type 14 PS (i.e. desialylated type III PS, filled squares); (4) GBS Ia PS which contains the same three-sugar side-chains as type III (open circles); (5) GBS III-HSA (identical to the coating antigen; filled triangles); and (6) human serum albumin (HSA; crosses).

Figure 16:
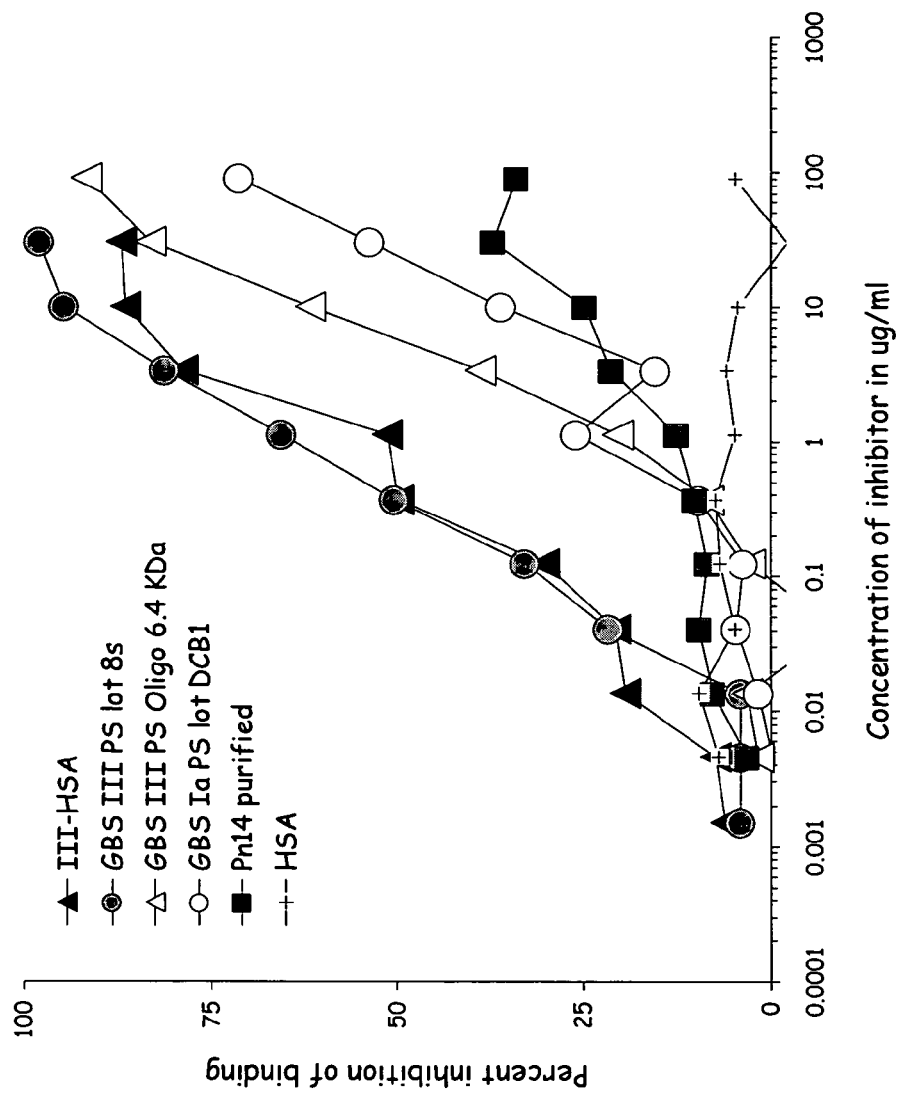
FIG. 16 is a graph depicting the inhibition of binding by IgG antibodies of macaque # 369 92 immunized with a GBS III-TT vaccine to native GBS III in the presence of: (1) native GBS III PS consisting of a polymer of approximately 150 repeat units (filled circles); (2) chemically modified GBS III PS representing reduced size type III oligosaccharide (OS) obtained by ozone treatment of the PS (open triangles); (3) full length Pneumococcal type 14 PS (i.e. desialylated type III PS, filled squares); (4) GBS Ia PS which contains the same three-sugar side-chains as type III (open circles); (5) GBS III-HSA (identical to the coating antigen; filled triangles); and (6) human serum albumin (HSA; crosses).

The inhibition results for serum from monkey # 369 92 is depicted in FIG. 16 and are representative for all three monkeys. FIG. 16 shows that all of the vaccine-induced antibodies recognized the native III PS (filled circles and filled triangles) while only a subpopulation of the antibodies recognized the desialylated type III PS (Pn14, filled squares). Furthermore, the dominant epitope is dependent on the size of the type III polymer, as the native GBS III PS (filled circles) is a much better inhibitor than a shorter version (type III OS, open triangles).

Figure 17:
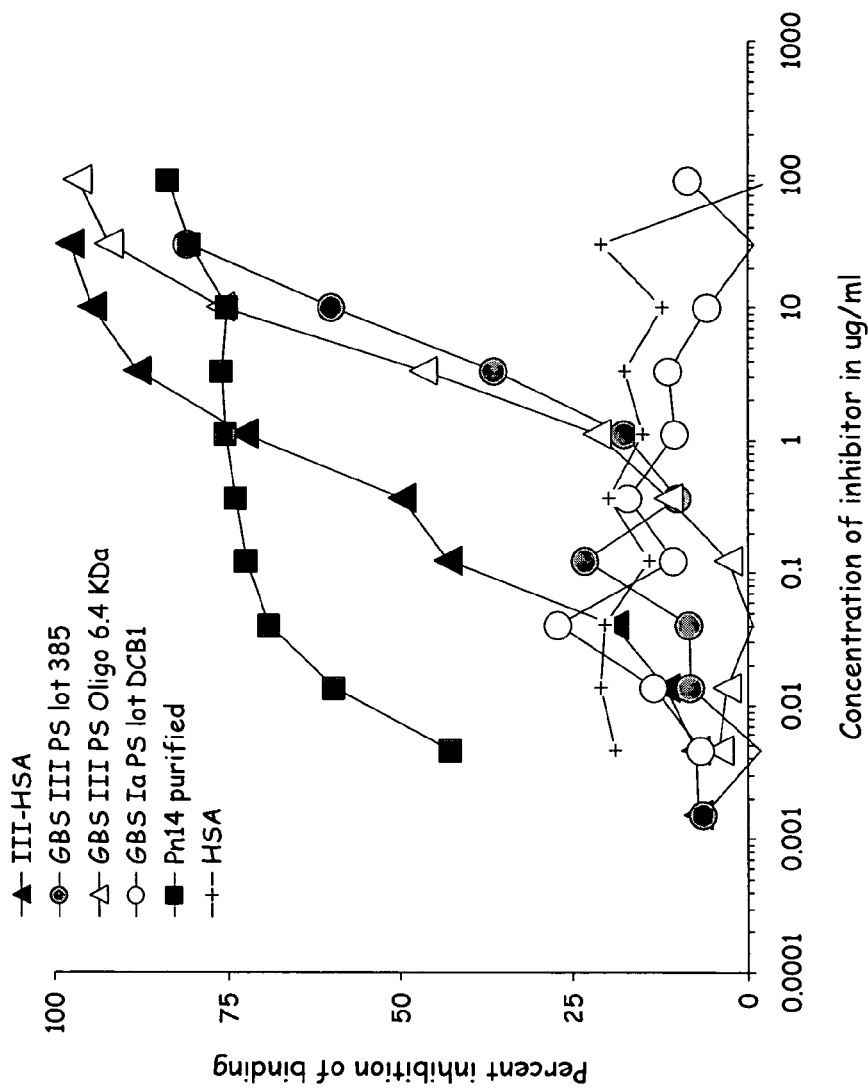
FIG. 17 is a graph depicting the inhibition of binding by IgG antibodies of macaque # 543 91 immunized with a GBS III-TT vaccine to native GBS III in the presence of: (1) native GBS III PS consisting of a polymer of approximately 150 repeat units (filled circles); (2) chemically modified GBS III PS representing reduced size type III oligosaccharide (OS) obtained by ozone treatment of the PS (open triangles); (3)

The population of type III-induced antibodies that recognized the desialylated type III (i.e. Pn 14, filled squares) varied among the monkey sera, as it does for human sera. In humans, approximately 50% of the vaccinees have vaccine-induced antibodies that recognize only the native type III PS while 50% have antibodies that also recognize the desialylated form of type III PS (elicited by GBS III PS given unconjugated or conjugated to tetanus toxoid). In humans, a subpopulation of the antibodies recognize Pn14, or the total antibody population is cross-reacting. The same was true for the monkeys. One of the monkeys did not have detectable Pn14-cross-reacting antibodies (data not shown), one had a subpopulation of antibodies that recognized Pn14 (monkey # 369 92, FIG. 16) and in monkey # 543 91, all of the vaccine-induced antibodies also cross-reacted with Pn14 (FIG. 17).

The IgM fraction of the type III-induced antibodies had the same specificity as the IgG fraction in all three monkeys (data not shown).

In summary, the B-cell epitope patterns observed for type III vaccine-induced antibodies in rhesus macaques are identical to those observed for human vaccinees.

Example 7

Specificity of GBS Type V-Induced IgG Antibodies in Rhesus Macaques

The B-cell epitopes recognized by GBS type V-TT glycoconjugate vaccine-induced antibodies in non-human primates were examined by competitive ELISA. The IgG fraction of vaccine-induced antibodies from one rhesus macaque immunized with GBS V-TT was allowed to bind to native GBS type V polysaccharide coated onto plastic 96 well plates in the presence of various amounts of free polysaccharides in solution. The results are plotted in FIG. 18, with the amount of inhibitors given in µg/ml along the X-axis on a logarithmic scale and the percentage inhibition of binding of the antibodies to the PS bound to the ELISA plates given along the Y-axis on a linear scale.

Polysaccharides tested for inhibition were: (1) native type V polysaccharide consisting of a polymer of approximately 200 repeat units conjugated to HSA (filled black triangles); (2) unconjugated GBS V (white triangles); (3) desialylated type V PS (filled squares); and (4) deaminated type V PS which contains the type V backbone with the one-sugar sidechain (circles); and (5) PGA (crosses).

All of the vaccine induced antibodies recognized the deaminated (circles) and the desialylated type V PS (squares) as shown by the overlapping inhibition curves for these chemically modified polysaccharides and the native type V PS (triangles)(FIG. 18).

Thus, the backbone of the GBS type VPS is the dominant epitope in macaques as well as in humans.

The dominant B cell epitope for the GBS V-TT vaccine-induced antibodies in rhesus macaques was the backbone of the polysaccharide. The tri-saccharide sialic acid containing sidechain was not part of this epitope. The results from the competitive inhibition ELISA for macaque # 256 89 are shown in FIG. 19. For this individual monkey, the antibodies bound substantially better to the deaminated type VPS than to the native PS.

The IgM fraction of the GBS type V-induced antibodies had the same specificity as the IgG fraction for all three monkeys (data not shown).

Example 8

Function of Type V-Specific Antibodies in Rhesus Macaques

Antibodies induced by vaccination of macaques with the GBS V-TT vaccine were tested for osponophagocytic killing as described in Example 2. The GBS V-specific antibodies were able to mediate killing of the GBS bacteria (FIG. 20). Both the IgG antibody fraction (gray bars) and the IgM antibody fraction (striped bars) of serum from macaque # 256 89 promoted killing of GBS V bacteria. We found that 1 µg/ml of GBS V-specific IgG and 0.1 µg/ml of GBS V-specific IgM promotes killing of more than 90% of the bacteria present in the reaction mixture. Thus the IgM fraction is more efficient in promoting killing of the bacteria. The white and speckled bars are controls included in each assay as part of the quality control of the experiments. The data for opsonophagocytic killing of group B streptococci in the presence of serum from macaque # 256 89 is representative for the antibodies induced in all three monkeys.

In summary, the results obtained in both humans and macaques indicate that the trisaccharide sidechain of the type V polysaccharide is not recognized by the immune system. It is possible that the sidechain with a sialic acid "masks" the recognizable immunodominant epitope of type V polysaccharides in humans and non-human primates. We hypothesized that providing the immunodominant epitope might improve stimulation of the immune system and allow for better isotype switching to protective PS-specific IgG antibodies. We designed a new experimental GBS V vaccine in which a chemically modified desialylated GBS V PS was conjugated to a protein carrier, and we examined whether this allowed for better recognition of a protective epitope (e.g., the backbone of the type V repeat unit including the glucose residue bound directly to the backbone) and thus allow for isotype switching to protective V-specific IgG.

Example 9

Vaccination of Rhesus Macaques with a Modified Type V-Polysaccharide-Protein Conjugate Purified GBS V PS was desialylated and oxidated to generate reactive aldehyde groups for conjugation to monomeric TT by reductive amination. The desialylated V-TT vaccine was non-toxic and immunogenic in mice. Next, the vaccine was tested for immunogenicity in non-human primates. Three rhesus macaques were injected twice, 8 weeks apart, with the desialylated V-TT vaccine. Serum was isolated from the animals to characterize epitope recognition and functional activity of antibodies induced in the animals.

GBS V-specific IgM antibody responses of three monkeys immunized with the desialylated GBS V-TT vaccine are depicted in FIG. 21. Each line represents the level of GBS V-specific IgM antibodies in an individual monkey before and after two immunizations with the desialylated GBS V-TT vaccine. The time in weeks after primary immunization is given along the X-axis and the levels of type V-specific IgM antibodies in µg/ml are given along the Y-axis. The immunizations are indicated by the black arrows.

None of the three monkeys immunized with the desialylated GBS V-TT vaccine had IgM antibodies to the native type V PS before the immunizations. A GBS V-specific IgM response was observed in all three animals after the first dose of the vaccine with peak levels observed 3-5 weeks after the immunization. GBS V-specific IgM levels did not increase after the second immunization. The GBS V-specific IgM levels induced by the desialylated GBS V-TT vaccine were lower than those induced by the native GBS V-TT vaccine, with a median level of GBS V-specific IgM of 5 µg/ml induced by the desialylated vaccine versus 30 µg/ml induced by the native vaccine, respectively. GBS V-specific IgA responses before and after two immunization with the desialylated GBS V-TT vaccine are depicted in FIG. 22. Low levels of IgA antibodies were seen in two of the three monkeys after both immunizations.

GBS V-specific IgG antibody responses are depicted in FIG. 23. None of the three monkeys immunized with the desialylated V-TT vaccine had pre-existing IgG antibodies to type V polysaccharides before the immunizations. Levels of IgG V-specific antibodies were substantial after the first immunization with peak levels obtained 3-8 weeks after the immunization. In addition, a significant booster response after recall vaccination with desialylated GBS V-TT was seen for all three monkeys. Thus, the desialylated V-TT vaccine stimulated a (1) moderate IgM response, (2) substantial IgG switching, (3) accelerated and increased magnitude of the V-specific IgG response after a second dose, and (4) a long lasting GBS V-specific antibody response, with median levels of V-specific IgG of approximately 10 µg/ml 10 weeks after the second vaccination.

Example 10

Specificity of IgG Antibodies Induced by a Modified Type V-Polysaccharide-Protein Conjugate The specificity of the IgG fraction of vaccine-induced serum antibodies obtained from rhesus macaque #259 87 was tested by measuring inhibition of binding to GBS V polysaccharides in the presence of desialylated, deaminated, or native GBS V polysaccharides. The results are depicted in FIG. 24 with the concentration of inhibitor depicted on the X-axis and percent inhibition on the Y-axis. All of the GBS V-specific antibodies produced in macaques immunized with the desialylated GBS V-TT vaccine induced IgG antibodies recognized the deaminated (circles) and the desialylated (squares) as shown by the similar inhibition curves for these chemically modified polysaccharides and the native type V PS (triangles). Thus, the dominant B cell epitope for the desialylated GBS V-TT vaccine-induced antibodies in rhesus macaques was the backbone of the polysaccharide with a side-chain glucose. The trisaccharide sialic acid-containing sidechain was not part of this epitope. The same results were obtained with serum from the other two monkeys.

The experiments were repeated for IgM antibodies from the macaques. The results for IgM antibodies for serum from macaque # 259 87 are depicted in FIG. 25. The vaccine-induced IgM antibodies recognized the deaminated (circles) and the desialylated type V PS (squares) as shown by the similar inhibition curves for these chemically modified polysaccharides and the native type V PS (triangles), thus the dominant B cell epitope for the desialylated V-TT glycoconjugate vaccine-induced antibodies in rhesus macaques was the backbone of the polysaccharide with a side-chain glucose. The tri-saccharide sialic acid containing sidechain was not part of the immuno-dominant B-cell epitope. The same results were obtained with serum from the other two monkeys.

Example 11

Function of Type V-Specific Antibodies in Rhesus Macaques

IgG and IgM fractions of antibodies from macaques immunized with the desialylated GBS V-TT vaccine were tested for opsonophagocytic killing in vitro. We found that antibodies of both the IgG and IgM fractions killed live GBS V streptococci in the presence of complement and PMNLs (FIG. 26).

Example 12

IgG Antibodies Induced by a Modified Type V-Polysaccharide-Protein Conjugate and Adjuvant.

A native GBS V-TT vaccine was administered to intraperitoneally to mice at doses of 0.625 µg PS per immunization and 6.25 µg PS per immunization. Mice were immunized with the GBS V-TT conjugate in the presence or absence of 0.5 mg of alum. Doses were administered at day 0 and day 21 to six 129/J mice per group. Sera were obtained from animals prior to immunization, between the first and second doses (at day 20) and after the second dose (at day 31). Levels of V-specific IgG induced in the animals of each group were determined by ELISA and are plotted in FIGS. 27A-27D. As shown in FIG. 27A, the concentrations of V-specific IgG induced by the low dose of the GBS V-TT composition 31 days after immunization were between 0.01 and 1 µg/ml. By contrast, the addition of alum resulted in levels of V-specific IgG between 10 and 100 µg/ml (FIG. 27B). Similarly, the high dose of GBS V-TT in the absence of alum induced 0.01-0.05 µg/ml of V-specific IgG (FIG. 27C), whereas the high dose induced levels of 10-100 µg/ml in the presence of alum. These data show that alum can enhance the immune response to GBS conjugate compositions in mammals.

Example 13

Protection of Neonatal Animals from Challenge Via Passive Maternal Immunization

A mouse model of maternal vaccination and neonatal challenge was used to examine the protective efficacy in vivo by passive immunization with sera obtained from macaques immunized with a desialylated GBS type V glycoconjugate vaccine. This model is described in Rodewald et al., *J Infect Dis.*, 166(3):635-9, 1992. Briefly, pregnant CD-1 mice (3 animals per group) were given a single intraperitoneal injection of 0.5 ml of one of the following plasma samples: pooled sera obtained from 3 macaques immunized with GBS V-TT; pooled sera obtained from 3 macaques immunized with after immunization with disialylated GBS V-TT; standard human reference serum pool (SHRSIII; positive control); or pooled preimmune macaque plasma (negative control). The concentration of GBS V-specific IgG in each serum/plasma pool is listed in Table 4.

TABLE 4

Concentration of GBS V-Specific IgG in Serum/plasma Pools Tested in GBS Passive Protection Model

| Serum/plasma pool | V-IgG (µg/ml) |
|---|---|
| Desialylated V-TT induced (pooled macaque plasma) | 12.3 |
| V-TT induced (pooled macaque plasma) | 10.5 |
| standard human reference sera V (V-TT induced; positive control) | 11.6 |
| pooled preimmune macaque plasma | not detectable |

Sera were administered to the mice 2-3 days before birth. On the first day of life, pups born to the mice were challenged with a dose of GBS (strain CJB111) 40 times greater than that which kills 50% of the mice in this model ($40 \times LD_{50}$). The numbers of pups surviving the GBS challenge 48 hours after birth are listed in Table 5. As shown in Table 5, passive vaccination of pregnant animals with sera from macaques immunized with desialylated GBS V-TT was effective in protecting their pups from lethal doses of GBS. Protection by sera from desialylated V-TT induced animals was comparable to protection by sera from V-TT induced animals.

TABLE 5

Survival of Pups in GBS Passive Protection Model

| Serum/plasma pool administered to mothers | Percent surviving (number surviving/total) |
|---|---|
| Desialylated V-TT induced (pooled macaque plasma) | 66% (20/30) |
| V-TT induced (pooled macaque plasma) | 78% (25/32) |
| standard human reference sera V (V-TT induced; positive control) | 73% (27/37) |
| pooled preimmune macaque plasma | 16% (3/18) |

Example 14

Protection of Neonatal Animals from Challenge Via Active Maternal Immunization

The mouse model of maternal vaccination and neonatal challenge described in Example 13, above, was also used to determine the in vivo efficacy of active immunization. V-TT or desialylated V-TT was administered to female CD-1 mice twice at days 0 and 21. Each dose contained 0.8 µg PS given as a glycoconjugate absorbed to aluminum hydroxide. Another set of female were administered saline and aluminum hydroxide, as controls. Pups born to the immunized mice were challenged on the first day of life with a dose of GBS (strain CBJ111) 40 times that lethal to 50% of the mice ($40 \times LD_{50}$) in this model. The numbers of pups surviving the GBS challenge 48 hours after birth are listed in Table 6. These data show that active immunization of females with desialylated GBS V-TT protects their newborn pups from lethal doses of GBS. Protection by active immunization with desialylated V-TT was comparable to protection by active immunization with V-TT.

TABLE 6

Survival of Pups in GBS Active Protection Model

| Vaccine administered to mothers | Percent surviving (number surviving/total) |
|---|---|
| Desialylated V-TT + alum | 98% (49/50) |
| V-TT + alum | 100% (71/71) |
| saline + alum | 41% (10/24) |

Other Embodiments

A number of embodiments of the inventions have been described. Nevertheless, it will be understood that various modifications may be made without departing from the spirit and scope of the inventions. Accordingly, other embodiments are within the scope of the following claims.

What is claimed is:

1. An antigenic composition comprising a purified desialylated group B streptococcus (GBS) type V polysaccharide, covalently linked to a polypeptide carrier moiety that facilitates T cell-dependent antibody responses to GBS type V polysaccharide, wherein the antigenic composition induces median serum IgG levels specific for native GBS type V polysaccharide higher than median serum IgM levels specific for native GBS type V polysaccharide when two doses are administered to a monkey.

2. The antigenic composition of claim 1, wherein the monkey lacks IgM antibodies specific for the native GBS type V polysaccharide prior to the administration of the first dose.

3. The antigenic composition of claim 2, wherein the antigenic composition induces the median serum IgG levels specific for the native GBS type V polysaccharide of approximately 10 µg/mL when the two doses are administered to the monkey.

4. The antigenic composition of claim 1, wherein the desialylated GBS type V polysaccharide is obtained by removing sidechain terminal sialic acid residues from a purified native GBS type V polysaccharide.

5. The antigenic composition of claim 4, wherein the desialylated GBS type V polysaccharide is obtained by treating the purified native GBS type V polysaccharide with 0.1 M sulfuric acid at 80° C. for 60 minutes.

6. The antigenic composition of claim 1, wherein the polypeptide carrier moiety is a bacterial polypeptide.

7. The antigenic composition of claim 6, wherein the bacterial polypeptide is a cell-surface or secreted polypeptide.

8. The antigenic composition of claim 1, wherein the polypeptide carrier moiety is a bacterial toxin or a bacterial toxoid.

9. The antigenic composition of claim 1, wherein the polypeptide carrier moiety is a tetanus toxoid.

10. The antigenic composition of claim 1, wherein the polypeptide carrier moiety is a diphtheria toxoid.

11. The antigenic composition of claim 1, wherein the polypeptide carrier moiety is diphtheria mutant protein cross-reactive material (CRM 197).

12. The antigenic composition of claim 1, wherein the composition further comprises a pharmaceutically acceptable carrier.

13. The antigenic composition of claim 1, wherein the composition further comprises an adjuvant.

14. The antigenic composition of claim 13, wherein the adjuvant is alum.

15. The antigenic composition of claim 4, wherein the desialylated GBS type V polysaccharide, is obtained by treating the purified native GBS type V polysaccharide with neuraminidase.

* * * * *

UNITED STATES PATENT AND TRADEMARK OFFICE
CERTIFICATE OF CORRECTION

PATENT NO. : 7,858,101 B2  Page 1 of 1
APPLICATION NO. : 11/264731
DATED : December 28, 2010
INVENTOR(S) : Dennis L. Kasper and Hilde-Kari Guttormsen It is certified that error appears in the above-identified patent and that said Letters Patent is hereby corrected as shown below:

Title Page; item (56);
Page 1, column 2 (other publications), line 28:
    delete "LraI." and replace with -- LraI --.

Signed and Sealed this
First Day of March, 2011

David J. Kappos
*Director of the United States Patent and Trademark Office*